(12) United States Patent
Watanabe

(10) Patent No.: US 8,125,632 B2
(45) Date of Patent: Feb. 28, 2012

(54) FABRICATION METHOD OF SEMICONDUCTOR INTEGRATED CIRCUIT DEVICE

(75) Inventor: Norio Watanabe, Moroyama (JP)

(73) Assignee: Renesas Electronics Corporation, Kanagawa (JP)

( * ) Notice: Subject to any disclaimer, the term of this patent is extended or adjusted under 35 U.S.C. 154(b) by 114 days.

(21) Appl. No.: 12/463,896

(22) Filed: May 11, 2009

(65) Prior Publication Data

US 2009/0221103 A1    Sep. 3, 2009

Related U.S. Application Data

(63) Continuation of application No. 12/106,438, filed on Apr. 21, 2008, now abandoned, which is a continuation of application No. 11/030,134, filed on Jan. 7, 2005, now Pat. No. 7,372,555.

(30) Foreign Application Priority Data

Jan. 23, 2004  (JP) ................................. 2004-015718

(51) Int. Cl.
    *G01N 21/00*  (2006.01)
(52) U.S. Cl. .................................. 356/237.1; 356/237.2
(58) Field of Classification Search .... 356/237.1–237.4, 356/239.1–239.8; 382/144–152
    See application file for complete search history.

(56) References Cited

U.S. PATENT DOCUMENTS

| | | | |
|---|---|---|---|
| 5,903,353 A | 5/1999 | Raymond | |
| 5,914,536 A | 6/1999 | Shizuki et al. | |
| 6,005,669 A | 12/1999 | Pahk et al. | |
| 6,040,895 A | 3/2000 | Haas | |
| 6,118,540 A | 9/2000 | Roy et al. | |
| 6,236,747 B1 | 5/2001 | King et al. | |
| 6,496,270 B1 | 12/2002 | Kelley et al. | |
| 2001/0013535 A1 | 8/2001 | Miyake et al. | |
| 2003/0001117 A1 | 1/2003 | Hyun | |
| 2004/0184653 A1 | 9/2004 | Baer et al. | |
| 2004/0213450 A1 | 10/2004 | Okada et al. | |

FOREIGN PATENT DOCUMENTS

| | | |
|---|---|---|
| JP | 05-296745 | 11/1993 |
| JP | 07-311025 | 11/1995 |
| JP | 8-327332 | 12/1996 |
| JP | 11-241916 | 9/1999 |
| JP | 2000-22326 | 1/2000 |

(Continued)

OTHER PUBLICATIONS

Chinese Official Action for Application No. 200510006203.2, dated Jul. 20, 2007.

(Continued)

*Primary Examiner* — Tri T Ton
(74) *Attorney, Agent, or Firm* — Antonelli, Terry, Stout & Kraus, LLP.

(57) ABSTRACT

In the fabrication of a semiconductor integrated circuit device, a 2D-3D inspection technique for solder printed on a substrate is provided which permits easy preparation of data and easy visual confirmation of a defective portion. In a substrate inspecting step, first, a 3D inspection is performed, followed by execution of 2D inspection, whereby a 2D picked-up image of the portion of a pad determined to be defective can be displayed on a larger scale simultaneously with the end of inspection, thereby providing an environment for efficient visual confirmation of the defect. Further, by subjecting a raw substrate to measurement at the time of preparing inspection data, a relation between an original height measurement reference generated automatically by the inspection system and the height of a pad upper surface is checked, whereby it is possible to measure the height and volume of printed solder based on the pad upper surface.

6 Claims, 29 Drawing Sheets

FOREIGN PATENT DOCUMENTS

JP 2000-193432 7/2000

OTHER PUBLICATIONS

Chinese Official Action issued on Mar. 8, 2010, for Application No. 200910126112.0.

Taiwanese Official Action dated Jul. 12, 2011, for TW Application No. 1002060324001.

Japanese Official Action dated Aug. 2, 2011, for JP Application No. 2009-250101.

Japanese Official Action dated Feb. 22, 2011, for JP Application No. 2009-250101.

FIG. 13

| PAD No. | XY COORDINATES | PAD XY WIDTH | REFERENCE AREA | REFERENCE VOLUME | DETERMINATION VALUE | INSPECTION ITEM | HEIGHT FROM REFERENCE PLANE | MEASURED VALUE | 2D DETERMINATION RESULTS | 3D DETERMINATION RESULTS | DEFECTIVE IMAGE |
|---|---|---|---|---|---|---|---|---|---|---|---|
| 8101 | 8102 | 8103 | 8104 | 8105 | 8106 | 8107 | 8108 | 8109 | 8110 | 8111 | 8112 |
| | | | | | | | | | | | |
| | | | | | | | | | | | |
| | | | | | | | | | | | |
| | | | | | | | | | | | |

FIG. 14

| FIELD No. | INSPECTION ITEM | CENTRAL XY COORDINATES | START XY COORDINATES | END XY COORDINATES | FIELD X SIZE | FIELD Y SIZE | PAD No. |
|---|---|---|---|---|---|---|---|
| 821 | 822 | 823 | 824 | 825 | 826 | 827 | 828 |
| | | | | | | | |
| | | | | | | | |
| | | | | | | | |

FABRICATION METHOD OF SEMICONDUCTOR INTEGRATED CIRCUIT DEVICE

CROSS-REFERENCE TO RELATED APPLICATION

The present application claims priority from Japanese patent application No. 2004-015718, filed on Jan. 23, 2004, the content of which is hereby incorporated by reference into this application. This application is a Continuation application of application Ser. No. 12/106,438, filed Apr. 21, 2008 now abandoned, which is a Continuation of application Ser. No. 11/030,134, filed Jan. 7, 2005 now U.S. Pat. No. 7,372,555, the contents of which are incorporated herein by reference in their entirety.

BACKGROUND OF THE INVENTION

The present invention relates in general to a technique for use in fabricating a semiconductor integrated circuit device; and, more particularly, the invention relates to a technique applicable effectively to an inspection process in which solder printed on a substrate is inspected in three dimensions (hereinafter referred to as "3D") and in two dimensions (referred to as "2D" hereinafter).

For example, in connection with the fabrication of a semiconductor integrated circuit device, solder inspecting techniques are described in Japanese Unexamined Patent Publication No. 2000-193432 (Patent Literature 1) and No. 2000-22326 (Patent Literature 2).

Patent Literature 1, in connection with a technique for measuring bumps formed on a silicon wafer, describes a technique that is used for measuring the height and area of solder in 2D and 3D and in which a 2D measurement step is added before or after a series of 3D measurements.

Patent Literature 2 describes a solder inspecting technique in which a pad surface on a substrate is measured in 2D, and whether the state of solder is good or bad is detected from the result of the measurement and also from the state detected after application of solder on the pad surface. Then, if the pad surface is error-free, it can be further inspected in 3D as a second step.

[Patent Literature 1]
Japanese Unexamined Patent Publication No. 2000-193432
[Patent Literature 2]
Japanese Unexamined Patent Publication No. 2000-22326

SUMMARY OF THE INVENTION

As a result of studies made by the present inventors in connection with a technique used in the fabrication of a semiconductor integrated circuit device, especially a technique for inspecting solder printed on a substrate, the following points have become clear.

The following description is provided in order of the considerations of (1) a positive method of detecting a height measurement reference in the measurement of the height and volume of printed solder, (2) a method for measuring the height and volume of printed solder based on a pad upper surface reference by a complete automatic setting, and (3) a 3D solder print inspection system that is suitable for producing a visual determination.

(1) A Positive Method of Detecting a Height Measurement Reference in the Measurement of the Height and Volume of Printing Solder:

In applying 3D inspection to a solder print inspection device, a difficult problem is encountered in that an actual object to be inspected often involves substrate that is warped that, between an upper surface of the printed solder and the substrate surface (resist surface), there is a significant difference of about 100:1 at most in terms of the lightness value on an area image of a slit light-applied portion.

According to a conventional technique, as a countermeasure to the above-stated problem, a Z-axis mechanism is added to vertically actuate a laser and a PSD (Position Sensitive Detector) so as to follow the warped surface of the substrate. As to the difference in lightness (difference in reflectance) between the printed solder and the substrate surface, a measure is taken in which two PSDs are mounted, one being a PSD used for the detection of light reflected from the printed solder and the other being a PSD used for the detection of light reflected from the substrate surface. According to this technique, however, there arises a problem of increased cost because two PSDs are required.

(2) A Method of Measuring the Height and Volume of Printed Solder Based on a Pad Upper Surface Reference by a Complete Automatic Setting:

For example, according to the conventional method, in preparing data for 3D inspection, it has been essential for a worker to perform an operation for setting a height measurement reference point. More particularly, the substrate upper surface, after creamy solder printing, is made up of cream solder, gold-, copper- or solder-coated pads (little exposed pads hidden by printed solder), resist which covers a base material directly from above, and resist which covers wiring patterns from above.

In this case, by reading gerber data (design data describing aperture shape, area and position), it is possible to know to which position on the substrate creamy solder has been transferred and in what amount it has been transferred. The inspection system being used measures an area in which creamy solder is to be transferred and can thereby measure the height of an upper surface of the printed solder as a value from a measurement reference of the inspection system. However, the height of printed solder must be measured from the upper surface of a pad.

If the substrate is completely rigid and free of any warp, it is possible to make the measurement reference of the inspection system and the upper surface of each substrate pad coincide with each other. In an actual substrate, however, there will be a warp of about ±1.5 mm at most, and, therefore, it is impossible to let the measurement reference of the inspection system and the upper surface of each substrate pad coincide with each other beforehand.

As a result, at the time of inspection, measurement of a pad upper surface, which is to be used as a measurement reference, is required separately from the measurement of the upper surface of the printed solder. Besides, when the presence of substrate warp is considered, it is necessary that a height measurement reference be established for each printed solder as an object of measurement and in the vicinity of the printed solder.

However, on the substrate after printing, the exposure of a pad upper surface is slight. A wiring pattern (inner layer pattern) covered with resist is considered as another reference plane, but the place on the substrate where the wiring pattern is present is limited.

A solder print inspection system usually does not have data showing the place where the inner layer pattern is present. Thus, in the conventional method, it is absolutely necessary for a worker to set a height measurement reference point.

(3) A 3D Solder Print Inspection System Suitable for Visual Determination:

A 3D inspection system usually does not have any means for picking up a 2D image, and, therefore, it cannot provide a worker with an enlarged image of an object, which is necessary for visual confirmation. On the other hand, in a combined 2D and 3D inspection machine, a 2D enlarged image of a portion which has been determined to be defective in 3D inspection can be provided to a worker. However, even in the combined 2D-3D inspection machine, the provision of such an enlarged image is very difficult, if the machine follows the sequence of first conducting 2D inspection and then conducting 3D inspection.

For example, in an inspection system incorporated in a production process, the storage of a picked-up image is usually not performed. This is because image data tends to be of large capacity, so that, if such data is to be stored, a time is required which is not negligible writing the data into a storage device; besides, the data will occupy a considerable portion of the storage device, and, thus, the storage thereof is not practical.

Therefore, only a portion of the data of a picked-up image, that has been determined defective by an inspection system to concern a defect, is stored as necessary. In this case, if 2D inspection is conducted first, and, thereafter, 3D inspection is conducted, then, in the case of an object to be inspected which is found to be defective in 3D inspection, but is determined to be good in 2D inspection, the 2D image is not stored. Consequently, when the inspection is completed, it is impossible to provide a 2D picked-up image that is necessary for a worker's visual confirmation.

In the above-stated case, for the provision of a 2D image for visual confirmation, it is necessary to perform an image pickup operation using a 2D camera once more with respect to a pad which has been determined the defective in 3D inspection and good in 2D inspection. Thus, a problem in that, during this image pickup operation, it is impossible for the worker to make a visual confirmation.

It is an object of the present invention to provide a 2D-3D inspection technique for solder printed on a substrate, which technique permits easy preparation of data and easy visual detection of a defective portion.

The above and other objects and novel features of the present invention will become apparent from the following description and the accompanying drawings.

Typical modes of the present invention as disclosed herein will be outlined below.

The present invention is applied to a method of fabricating a semiconductor integrated circuit device, comprising the steps of printing solder onto a substrate, inspecting the solder printed onto the substrate, and mounting circuit components onto the solder printed on the substrate. The inspection step comprises the steps of inspecting in 3D the solder printed on the substrate, inspecting in 2D the solder printed on the substrate, and displaying a defective portion in the 3D inspection on a larger scale in 2D. Thus, both the 2D inspecting function and the 3D inspecting function are provided, and 3D inspection is followed by 2D inspection, whereby a 2D picked-up image of a pad (printed solder) determined to be defective can be displayed on a larger scale simultaneously with the end of inspection. Hence, it is possible to provide a worker with an effective visually confirmed environment at the time.

The present invention is also applied to a method of fabricating a semiconductor integrated circuit device, comprising the steps of printing solder onto a substrate, measuring a raw substrate before solder printing in three dimensions to determine a reference plane in the height direction from an upper surface of a pad, inspecting the solder printed on the substrate on the basis of the reference plane, and mounting circuit components on the solder printed on the substrate, (including measuring a vertical positional relation between an exposed pad upper surface on the substrate before printing solder and at least another unsoldered portion on the substrate upper surface and calculating the height from the pad on the basis of the measured data with respect to an actually solder-printed substrate). Thus, at the time of preparing inspection data, a raw substrate before solder printing is subjected to a measurement to check the relation between an original height measurement reference produced automatically by an inspection system and the height of a pad upper surface, whereby the height and volume of printed solder based on a pad upper surface can be measured in the inspection.

Effects obtained by the typical modes of the present invention as disclosed herein will be outlined below.

It is possible to provide a 2D-3D inspection technique for solder printed on a substrate, which technique can omit manual inspection data preparing work so as to reduce the cost for preparing data and facilitate a visual confirmation of a pad that has been determined to be defective, thereby improving the total efficiency thereof as a man-machine system and reducing the operation cost.

BRIEF DESCRIPTION OF THE DRAWINGS

FIG. 13 is a diagram which shows a basic structure of inspection data (pad data) in a solder print inspection system;

FIG. 14 is a diagram which shows a basic structure of field allocation data in the solder print inspection system;

DETAILED DESCRIPTION OF THE PREFERRED EMBODIMENTS

Figure 1:
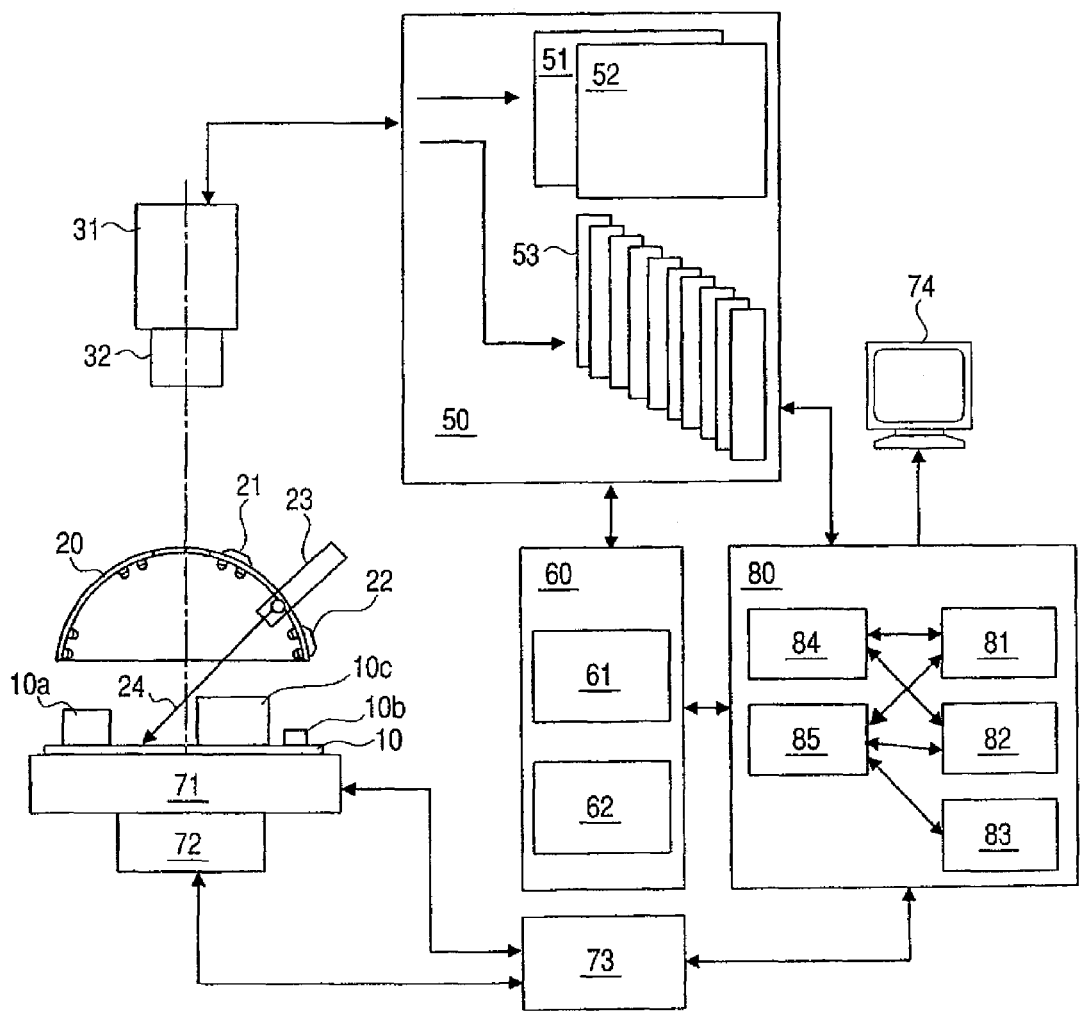
FIG. 1 is a diagram showing the overall configuration of a 2D-3D solder print inspection system (a single lens camera) used in an embodiment of the present invention.

In the following description of the embodiments, the same or similar parts will be identified by the same reference numerals, and repeated explanations thereof will be omitted in principle except where required.

Where required for convenience' sake, the subject matter of this invention will be described in a divided manner into plural sections or embodiments, but unless otherwise mentioned, they are not unrelated to each other, but are in a relation such that one is a modification, a detailed description, or a supplementary explanation, of part or the whole of the other.

In the following description of the embodiments, when reference is made to a number of elements (including the number, numerical value, quantity, and range), no limitation is made to the number referred to, but numerals above and below the number referred to will do as well, unless otherwise mentioned, and except for the case where it is basically evident that a limitation is made to the number referred to.

It goes without saying that, in the following description of the embodiments, constituent elements thereof (including constituent steps) are not always essential, unless otherwise mentioned, and except for the case where it is basically evident that the constituent elements are essential.

Likewise, it is to be understood that when reference is made to the shapes and positional relation of components in the following description of the embodiments, those substantially the same as or resembling such shapes, etc. are also included, unless otherwise mentioned, and except for the case where a negative answer obviously results. This is also true of the foregoing numerical value and range.

By the term "semiconductor integrated circuit device" as referred to herein is meant to include not only conventional semiconductor integrated circuit chips, but also electronic devices, each carrying, on a wiring substrate, one or plural semiconductor integrated circuit chips or electronic parts (electronic elements).

The following subjects (1) to (4), which are features of the present invention, will be described successively in this order: (1) a principle of measuring the height and volume of printed solder, (2) a positive method of detecting a height measurement reference in the measurement of height and volume of printed solder, (3) a method of measuring the height and volume of printed solder based on a pad surface by a complete automatic setting, (4) a 3D solder print inspection method suitable for visual determination.

(1) A Principle of Measuring the Height and Volume of Printed Solder:

In an inspection system according to the present invention, slit light is radiated to an object of measurement obliquely from above, and the state of the object is photographed by an area camera. Image pickup elements, such as CMOS transistors, MOS transistors, or CCDs, are arrayed and the object of measurement is photographed in the form of an area by such arrayed image pickup elements. It goes without saying that no limitation is made to the area camera, but any other camera is employable insofar as the camera used can eventually provide a two-dimensional image. The area camera is installed just above the object of measurement to measure the height and volume of the object of measurement.

It is preferable that the slit light have a length of not smaller than the field width of the area camera and that the slit width be about five pixels in terms of camera pixels. In case of using a camera of 1024 pixels×1024 pixels at a resolution of 20 μm/pixel, the size of the slight light is the minimum length 20.48 mm×width 0.1 mm.

If the slit light is inclined 45° from a substrate surface, the position of the slight light on an upper surface of the printed solder, which is imaged on the area camera, and the position of slit light on the substrate are deviated from each other by an amount corresponding to the height of the solder. By measuring the amount of this deviation, the height of the slit light-applied portion from the substrate can be measured.

With this measurement alone, there is obtained only height information of the slit light-applied segment portion. To avoid such an inconvenience, the area camera and the unit of slight light are moved relatively with respect to the object of measurement, and a large number of images that are slightly different in slit light-applied position are picked up. The image pickup spacing is set in such a manner that one image is picked up at every movement by a distance corresponding to the resolution of the optical system being used. From those large number of images, it is possible to measure the heights of various points at the surface of the object of measurement. Integrating this height information gives a volume value.

In general, the creamy solder print height is 100 to 160 μm. It is presumed that even the thickest value will not exceed 200 μm. Therefore, the positional deviation of slit light does not exceed 200 μm, either. This corresponds to ten pixels on the area camera, under the condition that an image is picked up at a resolution of 20 μm/pixel.

Thus, an image pickup range using the area camera may be a laterally long region matching the shape of the slit light. As an example, in case of a resolution of 20 μm/pixel, if an image is picked up in a range of 1024 pixels wide by 32-256 pixels long, it is possible to measure the height and volume of printed solder on the substrate. By minimizing the image pickup range in the height direction of the area camera to match the height of printed solder, it is possible to shorten the processing time of the inspection system.

(2) A Positive Method of Detecting a Height Measurement Reference in the Measurement of Height and Volume of Printed Solder:

In case of measuring the height and volume of a region of 20.48 mm×20.48 mm at a resolution of 20 μm/pixel, 1024 rectangular images of 1024 pixels×32-256 pixels are picked up.

When picking up the first one sheet of image, an image pickup range having an expanded measurement range in the height direction is set, and the exposure time is made long so that the substrate upper surface can be detected. The height of the substrate upper surface is detected from the first sheet of image. On the basis of the result of the detection, the image pickup range of the second and subsequent sheets is shifted.

As to the second to 1023th sheets of images, the image pickup range in the height direction is set to a minimum range to match the height of printed solder and the exposure time is made short so that the solder upper surface can be detected. For the last 1024th sheet of image, the exposure time is again set to be long so that the substrate upper surface can be detected again.

With the first one sheet of image and the last 1024th sheet of image, it is possible to measure the height of the substrate upper surface at each of upper and lower ends of the 20.48 mm×20.48 mm region. From these measurement results it is possible to define a height measurement reference plane (substrate upper surface reference).

From the second to 1023th sheets of images, it is possible to measure the height of the upper surface of printed solder. If the previous result of the height measurement reference plane (substrate upper surface reference) is reflected in this measurement result, the measured value of the height of printed solder becomes equal to the value obtained by measurement from the substrate upper surface and is thus not influenced by warping of the substrate.

The following effects can be obtained by the above-described positive method for detecting a height measurement reference in the measurement of height and volume of printed solder.

In the conventional method a difficult problem is encountered that, in applying 3D inspection to solder print inspection, the actual substrate which serves as an object of measurement has a warp, that there is a great difference of a maximum of about 100:1 in terms of a lightness value on an area image of the slit light-applied portion between an upper surface of the printed solder and the substrate surface (resist surface). The technique of the present invention can solve this problem at a minimum additional cost.

More particularly, according to the 3D inspection technique, when detecting a height measurement reference plane (substrate upper surface reference), the image pickup range in the area camera is set wide, whereby it is possible to follow the warp of the substrate. If the sensor used has 1024×1024 pixels and has a resolution of 20 μm/pixel, it is possible to cope with a variation in substrate height which is as large as 20.48 mm in theory, when the image pickup range is set to a maximum range.

According to the technique of the present invention, 1024 sheets of slit light images are picked up for producing one 3D image. Since the image sheets each can be picked up one by one independently, structural advantage is achieved in that the exposure conditions can be changed easily. By utilizing this structural advantage, when picking up a slit image to be used for detecting a substrate upper surface, an exposure time matching the reflectance of the substrate upper surface can be set easily; while, when picking up a slit image to be used for detecting an upper surface of the printed solder, an exposure time matching the reflectance of the printed solder can be set easily.

Thus, with only the basic constructional units, it is possible to cope with the warp of the substrate and detect such markedly different objects in reflectance as the substrate upper surface and the printed solder.

(3) A Method of Measuring the Height and Volume of Printed Solder Based on a Pad Surface Reference by a Complete Automatic Setting:

In the solder print inspection system, two types of measurement systems, one being a 2D measurement system and the other a 3D measurement system, are provided. These measurement systems each may be completely independent, but when the cost of the entire inspection system is taken into account, a structure that is being capable of being shared as much as possible is desirable. Data for 3D inspection, like data for 2D inspection, can be produced from gerber data of a metal mask.

Aperture information (shape, area, position) of a metal mask is acquired from gerber data of the mask. Since the aperture information is the particular reference area and reference position information of printed solder transferred onto a pad on the substrate, the data in question will serve as the data for 2D inspection. From the data for 2D inspection, a worker is requested to designate a portion to be subjected to 3D inspection. Further, the worker is also requested to input thickness information concerning the metal mask.

The thickness of the metal mask is the reference height of the printed solder. Further, a reference volume can be calculated by multiplying the value of the reference area by this reference height. In this way, data for 3D inspection, including the values of the height and volume of the printed solder are obtained. In the final stage of preparation of substrate inspection data, the worker is requested to load a raw substrate (a substrate before printing of the creamy solder, with the pad upper surfaces being exposed to the substrate surface and the other portion of the substrate being covered with resist).

Since images are inputted through a camera, the 2D inspection is carried out in the unit of a field (field by field, which is an area-like range taken by the area camera, corresponding to a pickup range 40 for 2D inspection to be described later). In 3D inspection, there basically is no concept of field (visual field), but since 3D inspection is the inspection of a designated portion, a concept of a like field (a height measurement region 11 in which an image pickup range 41 for 3D inspection to be described later operates relatively with respect to the substrate as an object of measurement to make the measurement of height) is introduced. There is executed "field allocation (a process of determining a field position so that the object of measurement is received efficiently within one height measurement region 11)" in which inspection data already produced is re-arranged field by field.

3D inspection is carried out on the basis of field-allocated inspection data. First, substrate upper surface heights at upper and lower ends in the 3D measurement field are measured and a height measurement reference plane, which is original to the inspection system, is created on the basis of the result of the measurement. Then, on the basis of the inspection data, the height of a pad portion in the object of 3D inspection is measured. Since the object of measurement is a raw substrate, printed solder is not present in the measurement area, and, hence, it is the pad height that is under measurement.

In this way, it is possible to define the height of each pad relative to the height measurement reference plane (substrate upper surface reference) original to the inspection system. This information is recorded pad by pad within the inspection data. This work is repeated for all of the pads for which 3D inspection is designated. When the inspection has been completed for all of the pads, the preparation of inspection data is over.

In the inspection, the height and volume of printed solder, relative to the height measurement reference (substrate upper surface reference) original to the inspection system, are measured. Since height information of each pad, relative to the height measurement reference original to the inspection system, is contained in the inspection data, the results of having measured the height and volume of printed solder can be converted to the height and volume based on a pad surface which the customer desires.

According to the above-described method, in which the height and volume of printed solder based on a pad surface are measured by a complete automatic setting, the following effects can be obtained.

According to the conventional method, in preparing data for 3D inspection, it has been absolutely necessary for a worker to perform the work of setting a height measurement reference point. However, according to the technique of the present invention, a height measurement reference that is original to the inspection system is produced automatically. Then, by measuring a raw substrate before printing, the height of each pad upper surface relative to the height measurement reference that is original to the inspection system is correlated with the height measurement reference. As a result, in solder print inspection, the height of printed solder is measured from the height measurement reference that is original to the inspection system. The result of the measurement can be converted to the pad upper surface reference and then outputted.

Thus, by a mere recognition of the raw substrate at the time of preparing 3D inspection data, inspection data of the pad upper surface reference can be created completely automatically. Thus, the inspection data preparing time can be greatly shortened in comparison with the conventional inspection system.

(4) A 3D Solder Print Inspection Method Suitable for Visual Determination:

First, 3D inspection of a designated pad portion is carried out, and the result obtained is recorded in an inspection result storage area. Thereafter, 2D inspection for all the pads is carried out. As to pads determined to be defective in the 2D inspection, not only the results of various measurements, but also images picked up by a 2D camera, are recorded. Further, 2D picked-up images are displayed at a designated position on the display unit.

As to pads determined to be defective in the 3D inspection, not only the results of various measurements, but also images picked up by the 2D camera, are recorded.

Further, 2D picked-up images are displayed at a designated position on the display unit.

When inspection for all the pads is over, a shift is made to a visual confirmation mode with respect to a substrate which has been determined to involve a printing defect. Since the 2D images of the pads determined to be defective are displayed on a larger scale on the display unit, the worker can utilize the enlarged images in visual confirmation in the same manner as in the confirmation of a microscopic image.

According to the above 3D solder print inspection method, which is suitable for visual determination, it is possible to obtain the following effects.

According to the conventional sequence of first conducting a 2D inspection and then conducting a 3D inspection, in the case of an object of inspection which is found to be defective in the 3D inspection, but appears to be good in the 2D inspection, a 2D image thereof is not stored. Therefore, at the end of the inspection, a 2D picked up image, which his necessary for worker to obtain a visual confirmation, cannot be provided. However, according to the technique of the present invention, in which execution of 3D inspection is followed by 2D inspection, 2D enlarged images of all pad portions that have been determined to be defective are displayed on the display unit. Therefore, the worker can shift to visual confirmation simultaneously with the end of inspection.

Although the problem in question is concerned with only the sequence in which 3D inspection is conducted first and thereafter 2D inspection is conducted, however, according to this sequence, in comparison with the reverse sequence, the total tact of the inspection system, including the visual confirmation time, can be improved.

An embodiment of the present invention will be described below in detail with reference to the accompanying drawings. In all of the drawings, members having the same functions are identified by the same reference numerals, and a repeated explanation thereof will be omitted.

Figure 2:
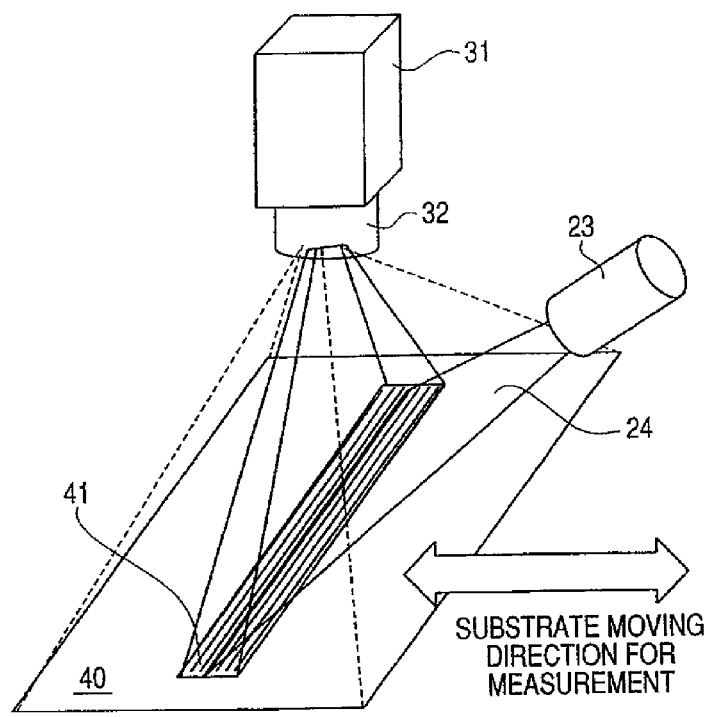
FIG. 2 is a diagram which shows a relation between a basic configuration of an optical system, which makes a 3D measurement, and an image pickup field.

First, with reference to FIGS. 1 and 2, an example of the construction and function of a 2D-3D solder print inspection system according to this embodiment will be described. FIG. 1 is a diagram showing the overall configuration of the 2D-3D solder print inspection system (a single lens camera), and FIG. 2 is shows the relation between a basic construction and an image pickup field of an optical system for conducting a 3D measurement.

As shown in FIG. 1, the 2D-3D solder print inspection device of this embodiment is provided with a lighting device 20. A reddish green LED lighting unit 21 for extracting a pad and a blue LED lighting unit 22 for detecting creamy solder are mounted on the lighting device 20. A slit lighting unit 23 is also incorporated in the lighting device 20. Slit light 24 is emitted from the slit lighting unit 23. The length of the slit light is about 30 mm and the width thereof is about 0.1 mm. Though not shown, the turning ON and OFF of the lighting units 21, 22 and 23 are controlled by an overall control section 80.

A lens 32 for forming an image onto an image pickup element and a camera 31 for converting the formed image into an electronic signal are installed above the lighting device 20. As to the camera 31, any type of camera will do so long as the camera used is an area camera. But, for conducting both 2D inspection and 3D inspection efficiently, a CMOS area camera (an area camera using a CMOS transistor as an image pickup element) is adopted in this embodiment. With this CMOS area camera, as shown in FIG. 2, when 2D inspection is performed, an image is picked up over an image pickup range 40 corresponding to the full range of the image pickup element. In the illustrated example, the camera is set so as to pick up an image over the range of 20.48×20.48 mm. In 3D inspection, an image is picked up while limiting the light to an image pickup range 41, including a portion to which slit light 24 is radiated. In the illustrated example, an image of only a required region in the range from 20.48×0.64 mm to 20.48× 5.12 mm is picked up. As to which range is to be subjected to image pickup processing, this is instructed by the overall control section 80 through an image input storage section 50.

The camera 31 is connected to the image input storage section 50 so that an output image from the camera 31 is inputted to the image input storage section 50. The image input storage section 50 is made up of an area of picked-up, solder image data 51 for 2D inspection, an area of picked-up pad image data 52 for 2D inspection, and an area of picked-up image data 53 for 3D inspection. In 3D inspection, a large number of images are picked up, while changing the position to which the slit light 24 is applied little by little, and therefore the picked-up image data 53 for 3D inspection is composed of a minimum of 1024 sheets of image data.

In 2D inspection, images picked up by turning ON only the blue LED lighting device 22 are stored in the area of picked-up solder image data 51 for 2D inspection. Images picked up by turning ON only the reddish green LED lighting device 21 are stored in the area of the picked-up pad image data 52 for 2D inspection.

In 3D inspection, only the slit lighting device 23 is turned ON and images limited in image pickup range to the image pickup range 41 for 3D inspection are picked up. The image data thereof is stored in the area of the picked-up image data 53 of 3D inspection. Further, picked-up images obtained by progressively changing the position to which the slit light 24 is applied are stored one after another as second, third, . . . sheets as the pick-up image data 53 for 3D inspection.

The image input storage section 50 is connected to an image processing section 60, so that an output from the image input storage section 50 is fed to the image processing section 60. The image processing section 60 includes an area of 3D measurement data 61 for storing height measurement data obtained by processing the picked-up image data 53 for 3D inspection provided from the image input storage section 50. The image processing section 60 further includes an area of 3D measurement data three-dimensional display 62 for the storage of three-dimensional display data from the 3D measurement data 61.

Solders 10a, 10b, and 10c are printed on the substrate 10 as an object of measurement. The substrate 10 is fixed onto an X-axis robot 71 which in turn is fixed onto a Y-axis robot 72. With operation of the X- and Y-axis robots 71, 72, the substrate 10 as an object of measurement can move relatively with respect to the lens 32 and the lighting device 20. In this way the camera 31 can pick up an arbitrary position on the substrate 10.

The X- and Y-axis robots 71, 72 are connected to a robot controller 73, which in turn is connected to the overall control section 80. As a result, the substrate 10 can move on the XY plane in accordance with instructions given by the overall control section 80. The overall control section 80 is used for controlling the constituent units of the inspection system. All of the robot controller 73, image processing section 60, image input storage section 50, and the lighting device 20 are constructed so as to operate in accordance with instructions provided from the overall control section 80.

Pad data 81, field allocation data 82, a picked-up data storage region 83, an inspection data preparing program 84, and an inspection execution program 85 are present within the overall control section 80. As to the functions thereof, a detailed description will be given later.

A display unit 74 is used for the display of information essential for the worker to operate the inspection system. Picked-up images are also displayed on the display unit 74.

Figure 3:
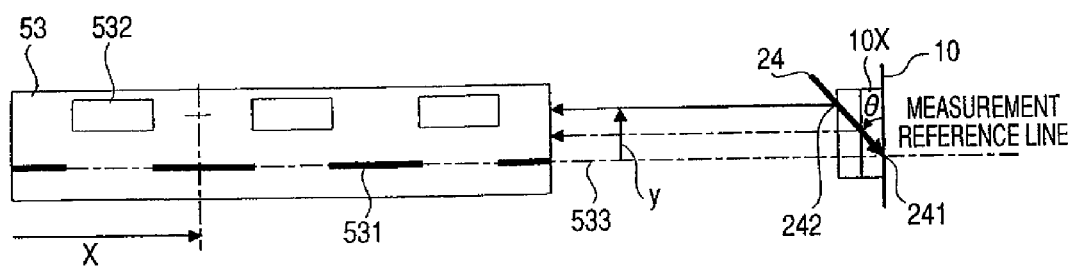
FIG. 3 is a diagram which shows a relation between the position at which slit light is applied to solder and the height of solder.
Figure 4A:
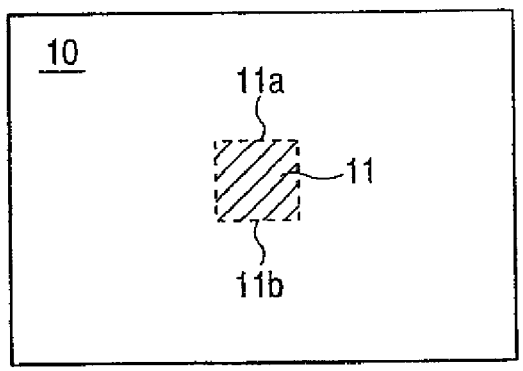
FIGS. 4(a) to 4(c) are diagrams which show a positional relation between a region on a substrate in which a 3D measurement is to be conducted and an image pickup field.
Figure 4B:
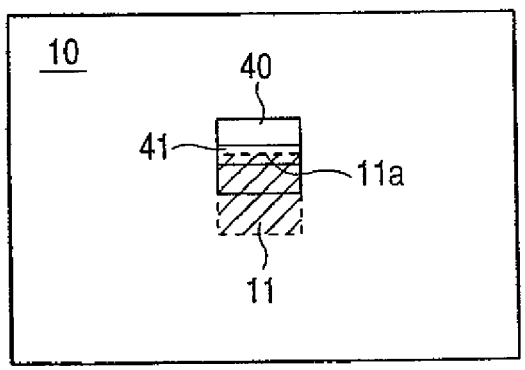
Figure 4C:
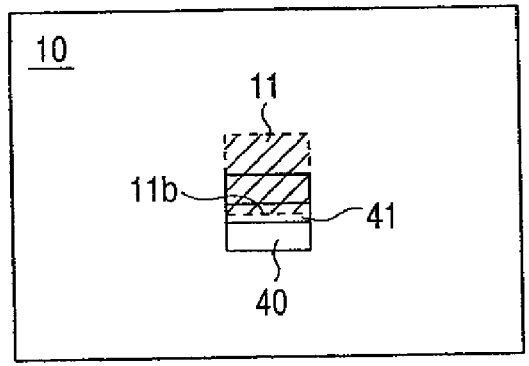
Figure 5:
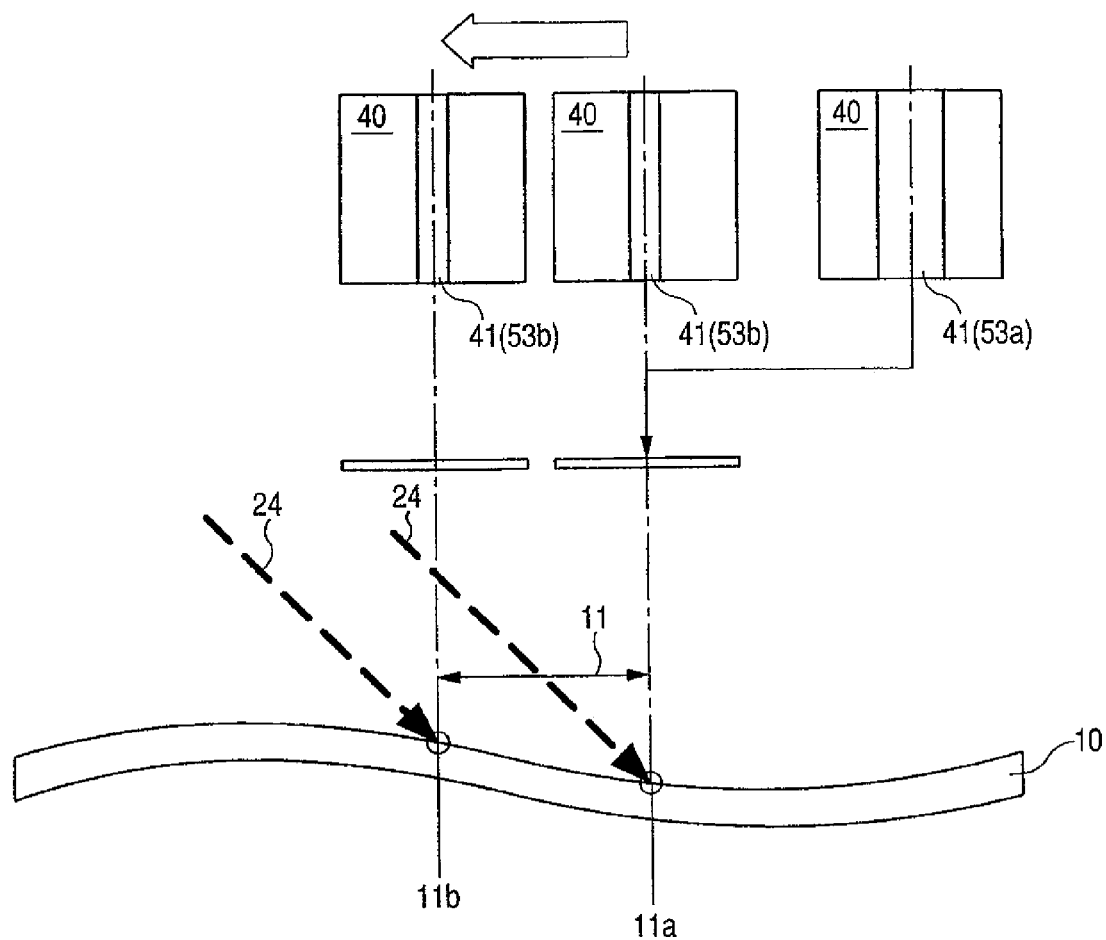
FIG. 5 is a diagram which shows a positional relation between a 3D image pickup region and an image pickup field relative to the substrate.
Figure 6:
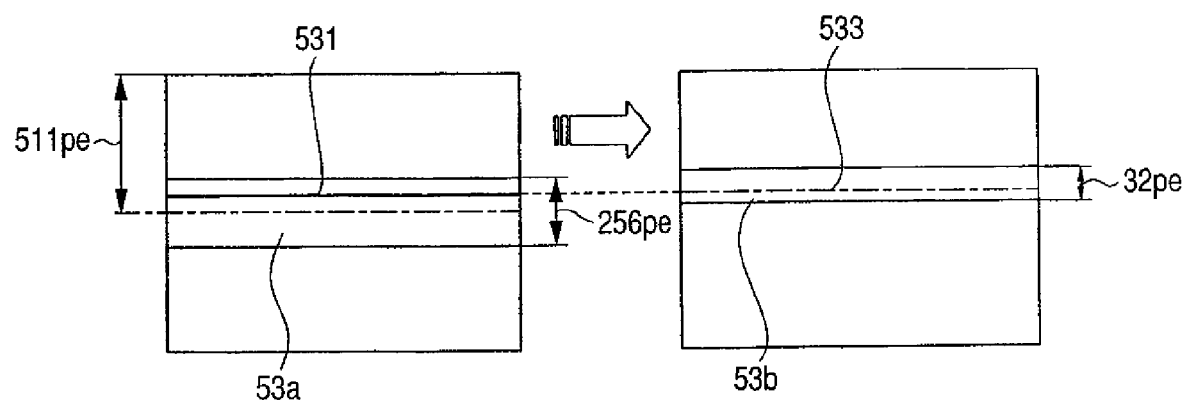
FIG. 6 is a diagram which shows a 3D image pickup region on an image pickup element of a camera.
Figure 7:
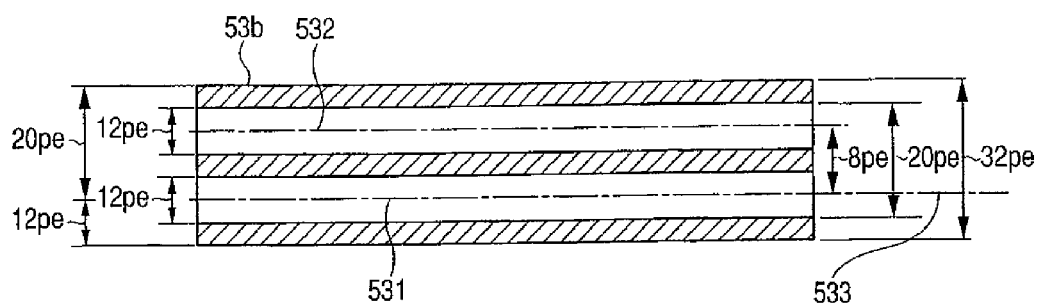
FIG. 7 is a cross-sectional view which shows how slit light is typically imaged in the 3D image pickup region.
Figure 8A:
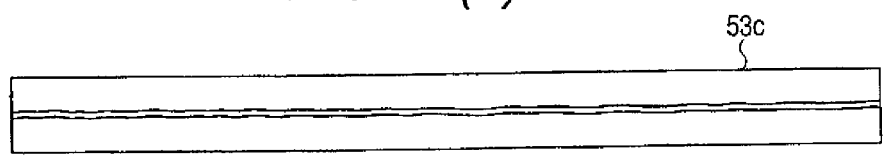
FIGS. 8(a) to 8(c) are diagrams which show how slit light is actually imaged in the 3D image pickup region.
Figure 8B:
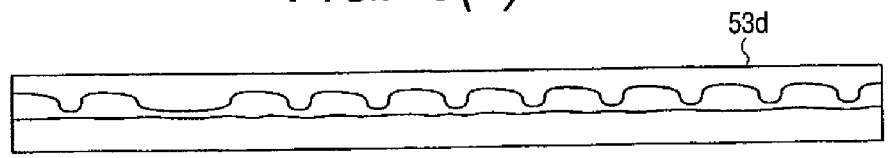
Figure 8C:
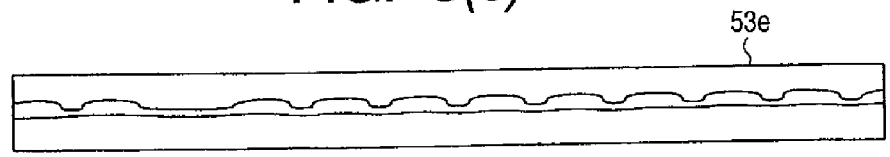
Figure 9:
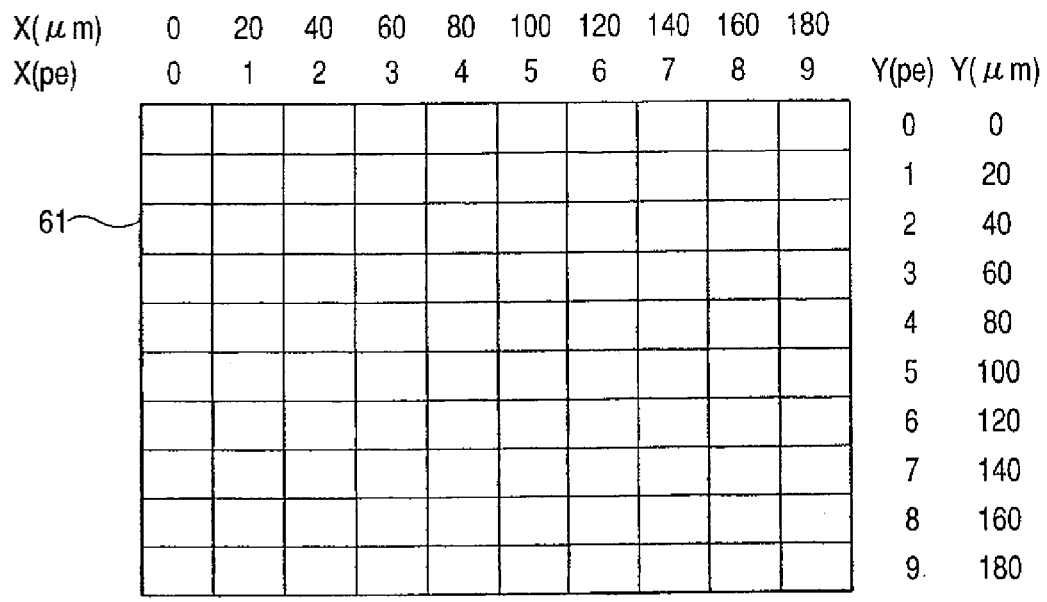
FIG. 9 is a diagram which shows the structure of a recording portion for storing the results of measurement of the height of an object of measurement from the position of slit light.
Figure 10:
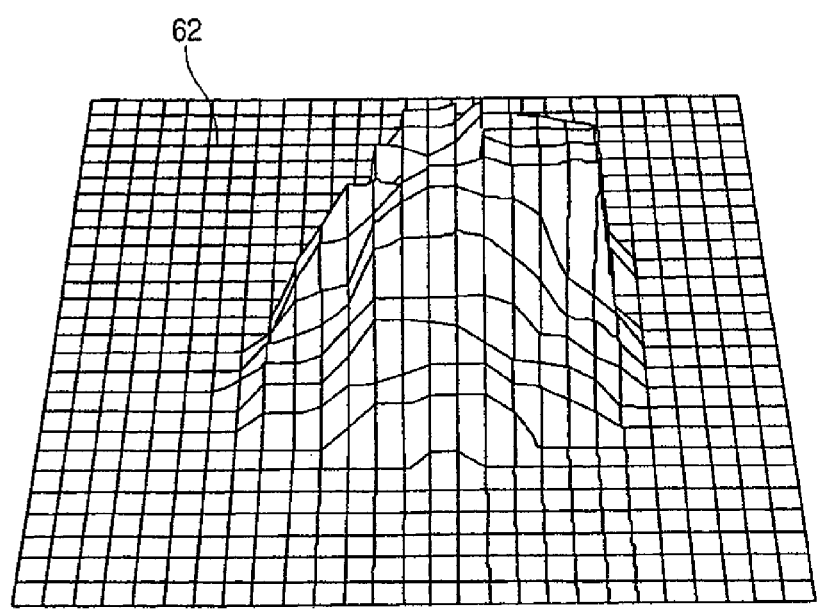
FIG. 10 is a three-dimensional graph which shows a reproduced 3D image of the object of measurement reproduced in CG from recorded height data of the object.

Next, an example of a principle of measuring the height and volume of printed solder in the 2D-3D solder print inspection system of this embodiment will be described with reference to FIGS. 3 to 10. FIG. 3 shows a relation between the position where slit light is applied to solder and the height of solder; FIGS. 4(a) to 4(c) each show a positional relation between a region on the substrate for which 3D inspection is to be conducted and an image pickup field; FIG. 5 shows a positional relation between a 3D image pickup region and an image pickup field relative to the substrate; FIG. 6 shows a 3D image pickup region on the image pickup element of the camera; FIG. 7 shows how slit light is imaged typically in the 3D image pickup region; FIGS. 8(a) to 8(c) show how slit light is actually imaged in the 3D image pickup region; FIG. 9 shows the structure of a recording portion for storing the results of having measured the height of an object of measurement from the position of slit light; and FIG. 10 shows a reproduced 3D image of the object of measurement reproduced from recorded height data of the object.

To make the essence of the present invention easier to understand, a description will be given mainly about 3D measurement of the height and volume of printed solder. For 3D and 2D measurement of printed solder, the technique disclosed in Japanese Patent Application No. 2003-106990, which the present inventors have filed previously, may be used.

In 3D measurement of the height and volume of printed solder, the X- and Y-axis robots 71, 72 are controlled so that slit light 24 is applied to the portion for measurement of height and volume in the 2D-3D solder print inspection system shown in FIG. 1.

As shown in FIG. 3 (the left side is a schematic plan view and the right side is a schematic sectional view (the indication of the section is omitted)), when slit light 24 is applied to the printed solder 10x (10a-10c) on the substrate 10 as an object of measurement, a slit light trace 242 is generated on the printed solder 10x and a slit light trace 241 is generated on the substrate 10. In the picked-up image data 53 for 3D inspection that has been picked up by the camera 31, the slit light trace 242 on the printed solder 10x is imaged as a slit light trace 532, and the slit light trace 241 on the substrate 10 is imaged as a slit light trace 531, in such a manner that their positions are deviated by an amount corresponding to the height of the printed solder 10x.

If the angle of slit light 24 from the upper surface of the substrate 10 is assumed to be $\theta$, the height of the printed solder 10x becomes equal to the value obtained by multiplying the deviation quantity by $\tan \theta$. On this basis, if a coordinate difference in the Y direction on the images of the slit light traces 532 and 531 is obtained from the picked-up image data 53 for 3D inspection and is then multiplied by $\tan \theta$, the height of the printed solder 10x can be determined.

However, with this measurement alone, it is only the height of the segment portion to which the slit light 24 has been applied that can be measured. It is impossible to measure the volume which is most required in the inspection of printed solder 10x. Therefore, the substrate 10 as an object of measurement is operated relatively with respect to the unit of camera 31 and slit lighting unit 23 for emitting the slit light 24. The operating direction is a direction orthogonal to the longitudinal direction of the slit light traces 241 and 242, i.e., the y direction in FIG. 3.

The range for 3D measurement on the substrate 10 as an object of measurement is set to a height measurement region 11, as seen in FIG. 4(a). First, as seen in FIG. 4(b), the X-axis robot 71 and the Y-axis robot 72 are controlled so that a height measurement reference line 11a representing an upper end of the height measurement region 11 lies within the image pickup range 41 for 3D inspection, which lies within the image pickup range 40 for 2D inspection. An image is picked up in the above-mentioned position, then the image pickup range 41 for 3D inspection is moved by 20 μm relatively with respect to the substrate 10, followed by pickup of an image, then the range 41 is further moved by 20 μm, followed by pickup of an image. Thus, these operations are repeated. Next, as seen in 4(c), a height measurement reference line 11b representing a lower end of the height measurement region 11 enters within the image pickup range 41 for 3D inspection, followed by repetition until pickup of an image.

FIG. 5 shows a positional relation between the position at which the height measurement reference line 11a of the upper end of the height measurement region 11 enters the image pickup range 41 and the position at which the height measurement reference line 11b of the lower end of the region 11 enters the image pickup range 41, with respect to the substrate 10 as an object of measurement. The image pickup range 41 for 3D inspection, which is present within the image pickup range 40 for 2D inspection, is moved leftward in FIG. 5.

If the range of the height measurement region 11 is assumed to be 20.48×20.48 mm, 20.4810.02=1024 sheets of data are picked up as picked-up image data for 3D inspection because image pickup is repeated in units of 20 μm. A portion of the image data actually picked up is shown in FIGS. 8(a) to 8(c). The actual image data 53c of FIG. 8(a) represents how the surface of the substrate 10 as an object of measurement is imaged; the actual image data 53d of FIG. 8(b) represents how a higher portion of printed solder 10x is imaged; and the actual image data 53e of FIG. 8(c) represents how a lower portion of printed solder 10x is imaged.

In the picked-up image data 53 for 3D inspection, a measurement reference line 533 is defined, as seen in FIG. 7. It is optional at which position of the image pickup region for 3D inspection the measurement reference line 533 is to be set. In this example, as shown in FIGS. 3, 6 and 7, the measurement reference line 533 is set substantially in conformity with the slit light trace 531 on the substrate, although the details thereof will be described later. The actual picked-up image data 53 for 3D inspection has a size of 1024 pixels (pe)×32-256 pixels (pe), with the number of picked-up images being 1024. To make the contents of subsequent processings easier to understand, as shown in FIG. 9, the size of the picked-up image data 53 is assumed to be ten pixels (0-9 pe: 0-180 μm) in the lateral direction (X direction), with the number of sheets of picked-up images being ten (in Y direction; 0-9 pe: 0-180 μm), as 3D measurement data 61.

First, as shown in FIG. 3, processing starts with the first sheet of picked-up image data 53 for 3D inspection. The y coordinates of the slit light traces 531 and 532 at x=0 pixel on the image are determined. Since the slit light 24 has a width of about 0.1 mm, it follows that, on an image, there is a width of at least five pixels. It is not that the five pixels have the same lightness value. The five pixels have a distribution such that the center is bright and the lightness becomes lower toward the outside. A lightness distribution in the width direction of the slit light 24 can be approximated accurately by determining a quadratic or quartic curve from the five pixels. By peaking this curve at y-coordinates, a y-coordinate value of slit light at x=0 can be determined accurately in the unit of one pixel or smaller. The y-coordinates are determined with the measurement reference line 533 as an origin.

By multiplying the y-coordinates by tan θ, the height of the slit light-applied portion from the measurement reference line is obtained. This processing is repeated from x=1 to x=9. Further, the same processing is repeated for the second to ninth sheets of picked-up image data 53 for 3D inspection. The end of all these operations means that the heights at all points in the height measurement region 11 have been measured. In this example, the measurement spacing is 20 μm in both x and y directions.

The measured height data is stored in the area of the 3D measurement data 61. The 3D measurement data 61 has a 2D matrix structure of (10, 10) so that height information of all the measured points can be recorded, as shown in FIG. 9. In connection with the case where the height data at x=n (n=0 to 9) of the mth sheet is yn×tan θ (n=0 to 9), a description will now be given to indicate into which cell of (10, 10) in the 3D measurement data 61 this data is to be written. Since x=n, it is evident that x coordinates are x=n. Because of the mth sheet, basic y coordinates are y=m. However, as is seen from FIG. 3, the point having a height of yn×tan θ lies at a position that is deviated by −yn in the y direction from the measurement reference line 533. Thus, the y-coordinates of the cell which stores the result becomes m-yn.

Since the 3D measurement data 61 is provided in a 2D matrix of (10, 10), the xy coordinate value of the cell becomes an integer multiple of the unit (20 μm in this example). Where the value of m-yn does not coincide with the integer value of the unit, the data of concern is written to the cell having the closest y-coordinate value. To sum up, when the y-coordinates of the slit light trace 532 at x=n of the mth sheet of picked-up image data 53 for 3D inspection are yn, its height data yn×tan θ is written to the cell (n, <m-yn>) of the 3D measurement data 61, provided <m-yn> is assumed to be "an integer multiple value of the unit" closest to m-yn.

In this way, 3D measurement data 61 of the height measurement region 11 is obtained. Since the measurement reference line 533 is aligned with the slit light trace 531 on the substrate, the 3D measurement data 61 will include concaves and convexes measured from the substrate upper surface. By integrating this data, volume data can also be obtained. Moreover, with 3D graphic processing, a three-dimensional display 62 such as in seen FIG. 10 can be obtained. In the three-dimensional display 62 of FIG. 10, the display portion having a lattice-like narrow line spacing represents a flat shape, while the display portion having a wide line spacing represents a convex shape, which portion corresponds to the printed solder.

Thus, 3D measurement can be carried out by the above-described constructions of FIGS. 1 and 2. In an actual solder printed substrate, however, there arises a great difference of a maximum of 100:1 in reflectance between the upper surface of printed solder and that of the substrate. Therefore, if an attempt is made to detect the upper surface of printed solder at an appropriate lightness, it becomes impossible to detect the substrate upper surface.

In the measurement described above, the measurement reference line 533 in the picked-up image data 53 for 3D inspection is placed in alignment with the slit light trace 241 on the substrate. If the substrate is free of warp or the like, the measurement reference line 533 and the substrate upper surface are always coincident with each other, so that a proper measurement of the height of the printed solder can be carried out even if the substrate upper surface cannot be detected.

However, an actual substrate 10 as an object of measurement warps by about ±1.5 as a maximum. In the presence of such a warp, the measurement reference line 533 and the substrate upper surface are not aligned with each other, with the result that the height measurement reference is lost. A solution to this problem will be described below.

Next, with reference to FIGS. 3 to 7, a description will be given of an example of a positive method for detecting a height measurement reference in the measurement of height and volume of printed solder using the 2D-3D solder print inspection system of this embodiment.

For permitting such a warp of the substrate 10 such as shown in FIG. 5, the image size of the picked-up image data 53 for 3D inspection is set at about 1024 pixels (pe)×256 pixels (pe) to obtain the picked-up image data 53a for substrate height measurement, as shown in FIG. 6. Since the resolution is 20 μm, the image pickup range 41 for 3D inspection becomes 20.48 mm×5.12 mm.

Since the slit light 24 is set at an angle of 45° relative to the substrate surface of the substrate 10 as an object of measurement, the image pickup range of 20.48 mm×5.12 mm is equal to a measurement range of 5.12 mm in the height direction. Taking into account the point that the height of printed solder is 0.2 mm as a maximum and the width of slit light is 0.1 mm, it is possible to ensure a measurement range in the height direction of about ±2.56–0.3 mm=±2.26 mm. Even with a margin, ±2.0 mm can be ensured. Thus, it is possible to fully cover ±1.5 mm of the warp of the substrate 10.

An image of the upper end portion of the height measurement region 11 is picked up in this image pickup range of the picked-up image data 53a for substrate height measurement. As shown in FIGS. 3 to 5, since the upper surface of the substrate 10 as an object of measurement is detected, the exposure time is set at 5 ms so as to give a sufficiently bright slit light trace 531 which permits detection of the slit light trace 241 on the substrate 10. Under this image pickup condition, the slit light trace 531 on the substrate is imaged at appropriate lightness and width. As to the slit light trace 532 on the printed solder 10x, this image pickup condition results in overexposure, resulting in the lightness becoming saturated and an image being picked up in a thickened state.

Thus, the two height information pieces, one being the upper surface of the substrate 10 as an object of measurement and the other being the upper surface of the printed solder 10x, are present in a mixed state. However, since it is evident that the lower one is the substrate upper surface, it is possible to easily specify a vertical position of the substrate upper surface (the slit light trace 531 on the substrate) on the height measurement reference line 11a.

Next, picked-up image data 53b for measuring the height of the printed solder is defined as shown in FIG. 6. The image size is set at 1024 pixels (pe)×32 pixels (pe) as shown in FIG. 7. Since the resolution is 20 μm, the image pickup range for 3D inspection becomes 20.48 mm×0.64 mm. A measurement reference line 533 is set at the position of the 12th pixel from below of the picked-up image data 53b. The picked-up image data 53b for measuring the height of printed solder is set at a position above the image pickup element of the camera so that the measurement reference line 533 comes into alignment with the vertical position (531) of the substrate upper surface on the height measurement reference line 11a.

The normal height of the printed solder 10x is 0.16 mm, which corresponds to eight pixels in the picked-up image data 53b. Consequently, a positional relation between the slit light trace 531 on the substrate 10 as an object of measurement and the slit light trace 532 on the printed solder 10x, in the picked-up image data 53b for measuring the height of printed solder, becomes a relation such as shown in FIG. 7.

With the picked-up image data 53b, 1022 sheets of images for detecting the upper surface of the printed solder are picked up at an exposure time of 0.05 ms. At such a short exposure time, only the slit light trace 532 on the printed solder 10x is imaged in the picked-up image data, with the slit light trace 531 on the substrate 10 not being imaged. The last 1024 sheets of images are picked up at a longer exposure time of 5 ms. Since the exposure time is thus made longer, it is possible to specify a vertical position of the substrate upper surface (the slit light trace 531 on the substrate) on the height measurement reference line 11b.

By applying the processing, based on the above-stated principle of measuring the height and volume of printed solder, to the second to 1023th sheets of picked-up image data 53b for measuring the height of printed solder, it is possible to measure the height of printed solder 10x on the basis of the measurement reference line 533. Besides, as noted previously, since the picked-up image data 53b for measuring the height of printed solder is set on the image pickup element of the camera so that the measurement reference line 533 becomes coincident with the vertical position (531) of the substrate upper surface on the height measurement reference line 11a, the measurement result obtained is one after correction of the warp of the substrate 10.

Further, since the upper surface height of the substrate on the height measurement reference line 11a and the upper surface height of the substrate on the height measurement reference line 11b are measured with respect to the first sheet of picked-up image, it is possible to detect the upper surface of the substrate (substrate warp, which, within this limited region, can be considered to be a substrate inclination) in the height measurement region 11. If the height measurement result of printed solder 10x is re-evaluated at the upper surface reference of the substrate 10 detected, a height measurement result of printed solder 10x, based on a more strict substrate upper surface reference, is obtained.

Thus, by controlling the image pickup range and the exposure time in detecting the upper surface of the substrate 10 as an object of measurement and by controlling the image pickup range and exposure time in detecting the printed solder 10x to respective optimal values, the height of the printed solder 10x can be measured on the basis of the substrate upper surface, without being influenced by the warp of the substrate 10. Besides, the extension of the measurement time for following up the warp of the substrate 10 can be kept to a minimum.

In the above description, it has been shown that the height of printed solder 10x can be measured on the basis of the upper surface of the substrate 10 as an object of measurement. To be more strict, however, it is necessary that the height measurement of printed solder 10x be determined on the basis of a pad upper surface. A specific method to achieve this will be described below.

Figure 11A:
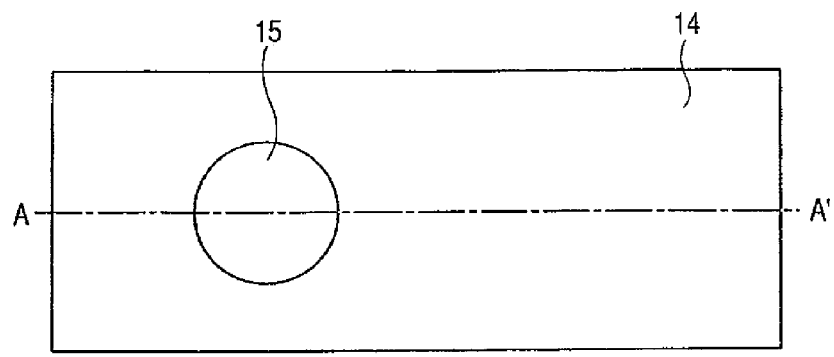
FIG. 11(a) is a plan view of the structure of a commonly-used substrate.
Figure 11B:
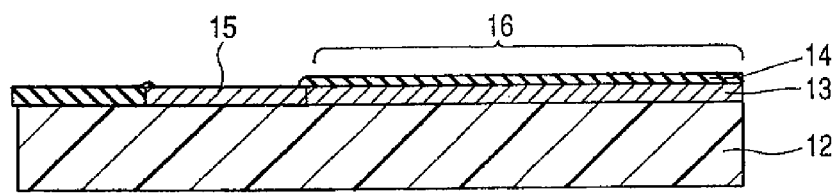
FIG. 11(b) is a section view taken along line A-A' in FIG. 11(a)
Figure 12:
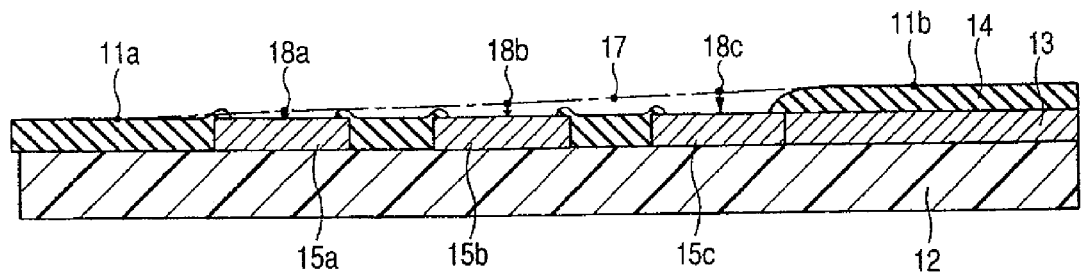
FIG. 12 is a cross-sectional view which shows a positional relation among a height measurement reference line, a height measurement reference plane, and a pad surface height.
Figure 15:
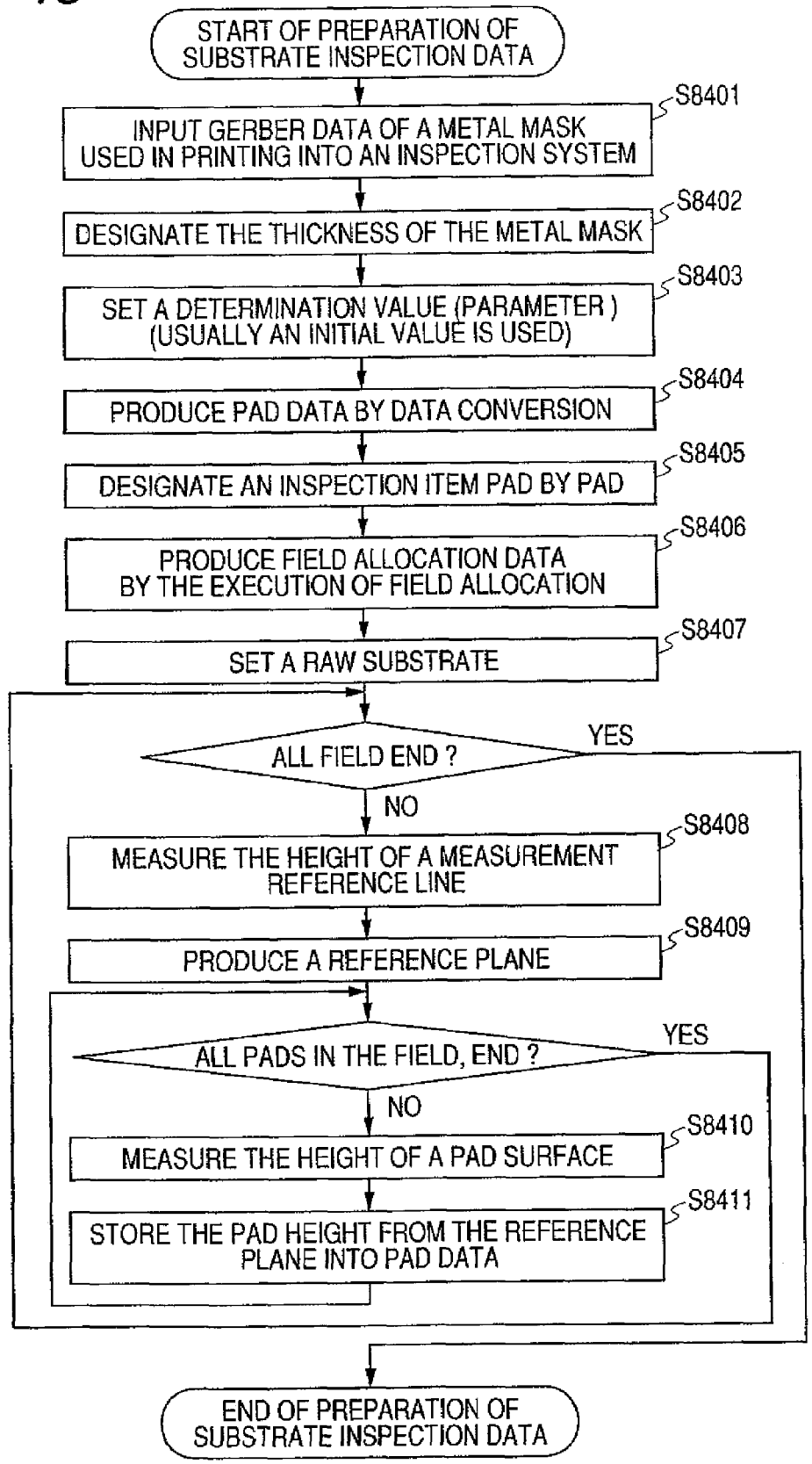
FIG. 15 is a flow chart showing a procedure for the preparation of substrate inspection data.
Figure 16:
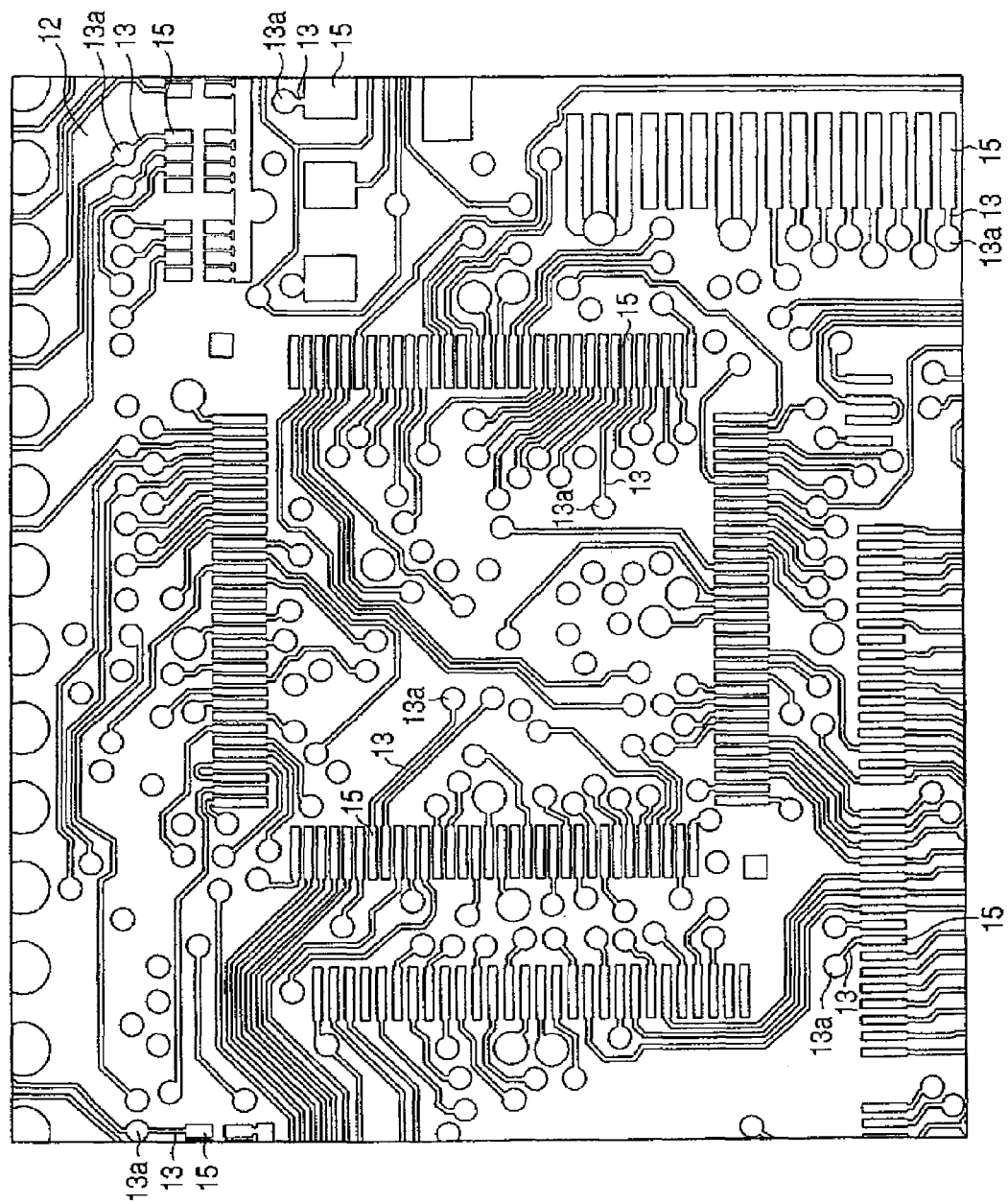
FIG. 16 is a top plan view which shows a base material of the substrate and wiring patterns.
Figure 17:
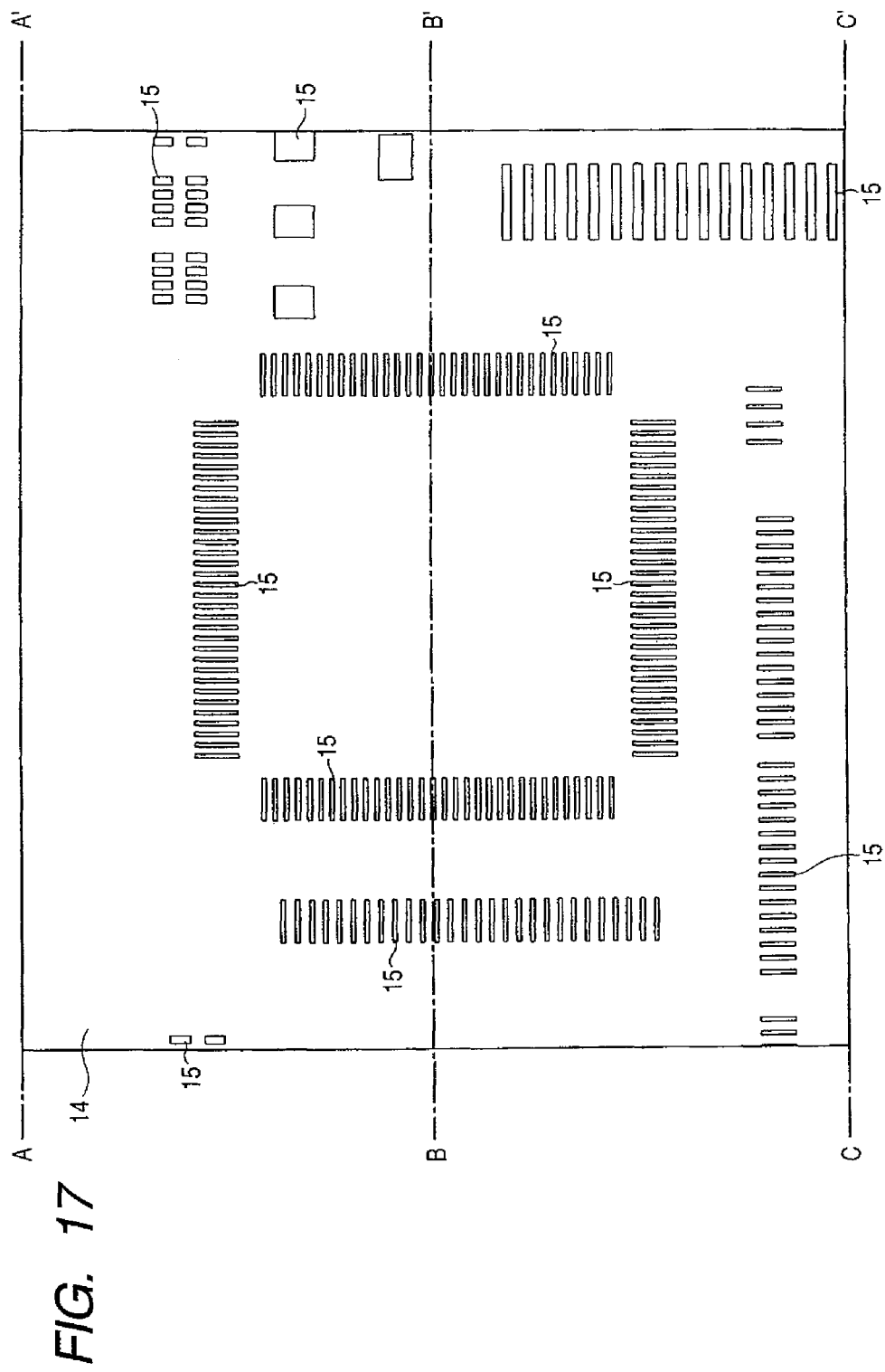
FIG. 17 is a top plan view which shows the structure and appearance of a commonly-used substrate composed of a base material, wiring patterns and resist.
Figure 18A:
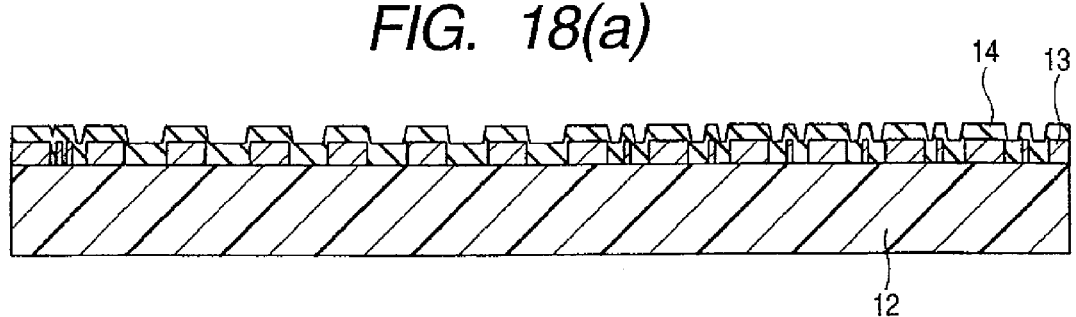
FIGS. 18(a) to 18(c) are section views taken along lines A-A', B-B', and C-C', respectively, in FIG. 17.
Figure 18B:
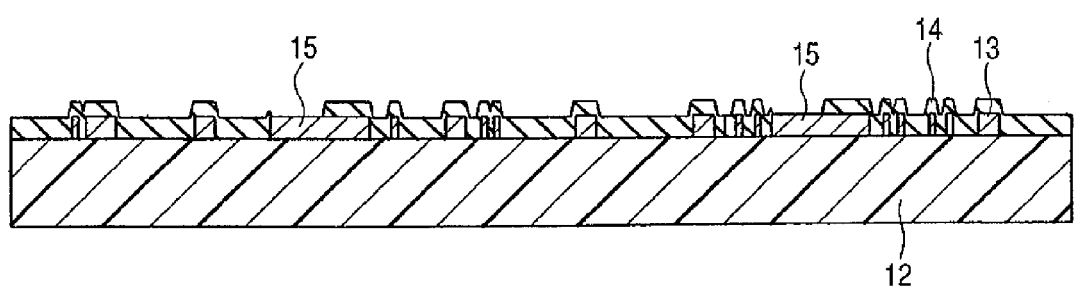
Figure 18C:
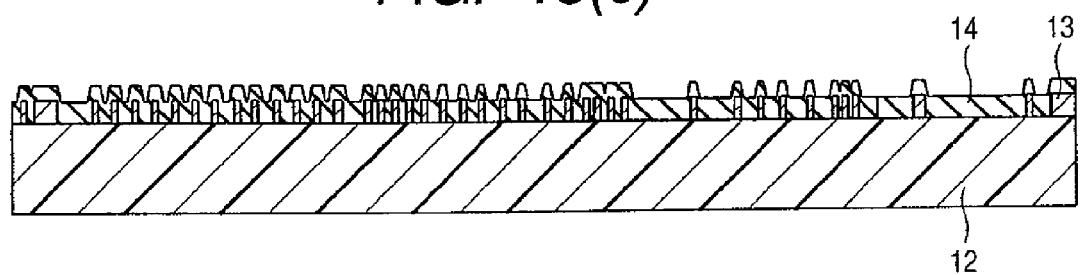
Figure 19:
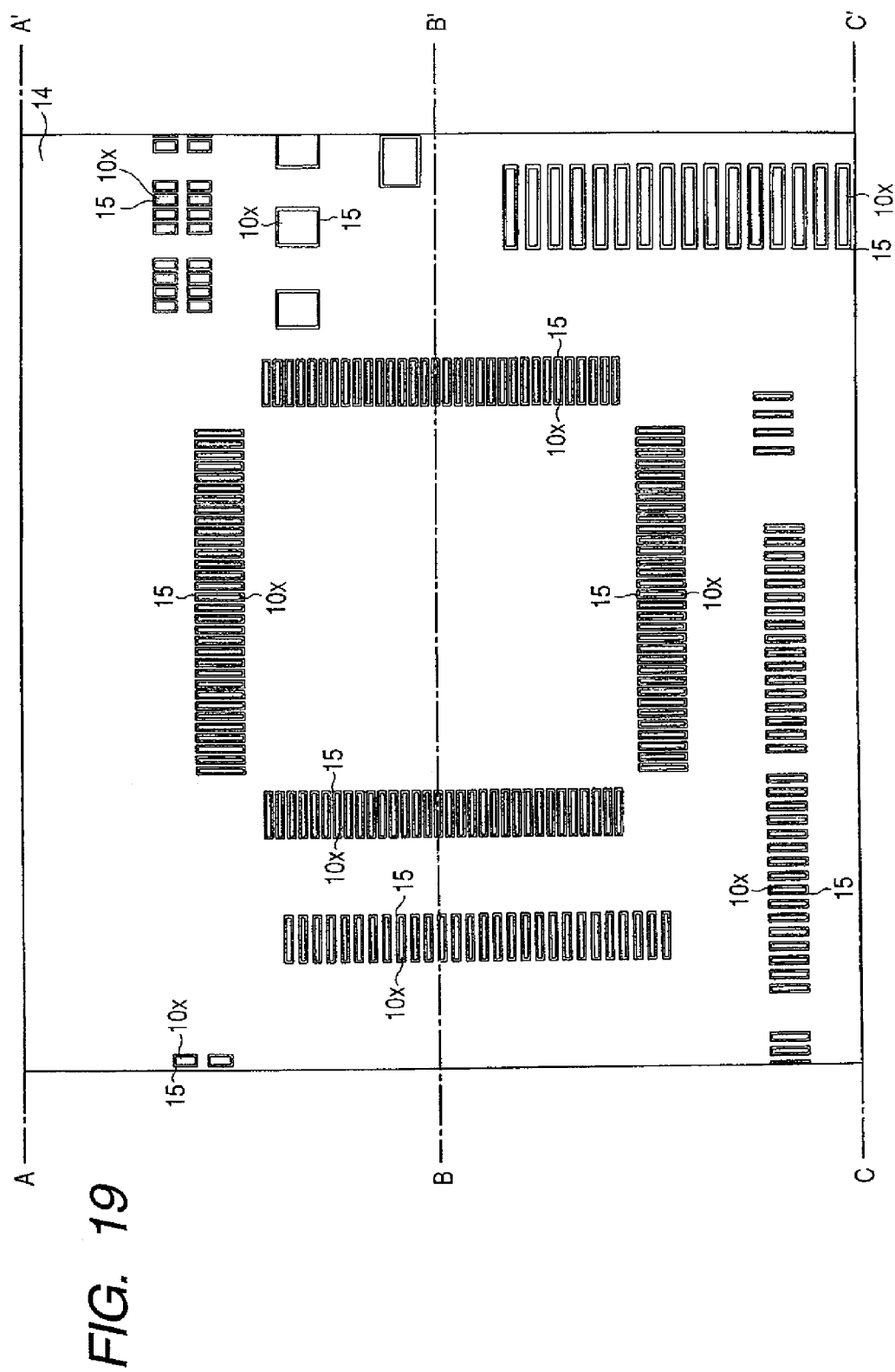
FIG. 19 is a top plan view which shows a state of creamy solder that has been transferred onto the substrate.
Figure 20A:
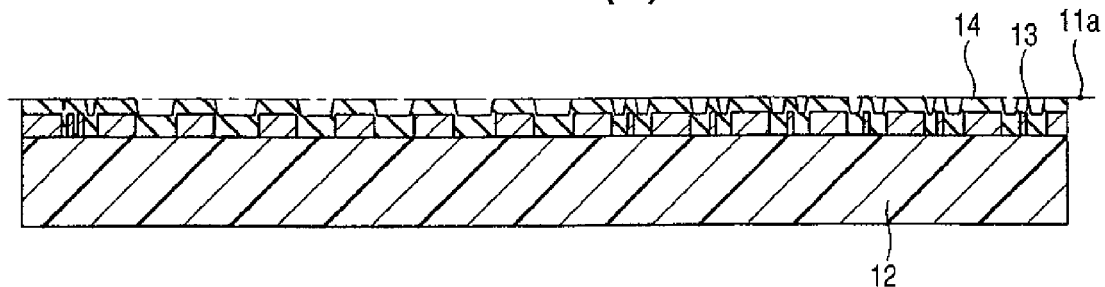
FIGS. 20(a) to 20(c) are section views taken along lines A-A', B-B', and C-C', respectively, in FIG. 19.
Figure 20B:
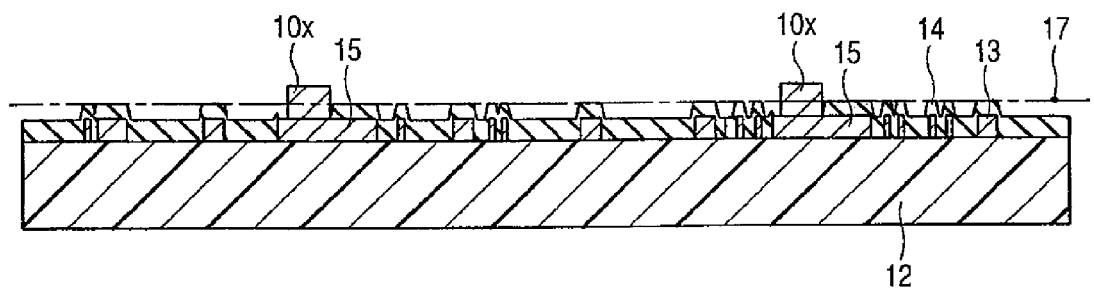
Figure 20C:
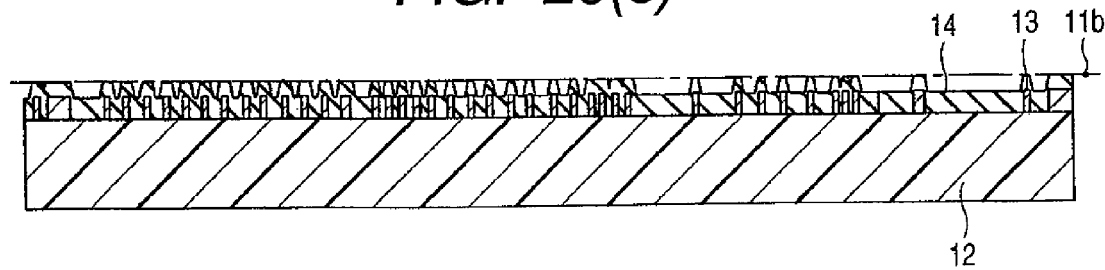

Next, with reference to FIGS. 11 (a) to 20(c), a description will be given below concerning an example of a method of preparing inspection data for measuring the height and volume of printed solder on the basis of a pad upper surface by a complete automatic setting in the 2D-3D solder print inspection system of this embodiment. FIG. 11(a) shows the structure of a commonly-used substrate and FIG. 11(b) is a section taken along line A-A', in FIG. 11(a). FIG. 12 shows a positional relation among a height measurement reference line, a height measurement reference plane, and a pad surface height. FIG. 13 shows a basic structure of inspection data (pad data) in the solder print inspection system. FIG. 14 shows a basic structure of field allocation data in the solder print inspection system. FIG. 15 is a flow chart showing a procedure for the preparation of substrate inspection data. FIG. 16 shows a base material of the substrate and wiring patterns. FIG. 17 shows the structure and appearance of a commonly-used substrate composed of a base material, wiring patterns and resist. FIGS. 18(a) to 18(c) are sections taken along lines A-A', B-B', and C-C', respectively, in FIG. 17. FIG. 19 shows a transferred state of creamy solder onto the substrate. FIGS. 20(a) to 20(c) are sections taken along lines A-A', B-B', and C-C', respectively, in FIG. 19.

According to the structure of a commonly-used substrate, as shown in FIGS. 11(a) and 11(b), wiring patterns 13 are formed of copper on a substrate base material 12. Portions of the wiring patterns 13 to be connected to terminals of mounted parts are exposed as they are as pad portions 15, which, as the case may be, are plated with gold for enhancing the electrical conductivity thereof. In each wiring pattern 13, the other area than the pad portion 15 is covered with resist 14 and is insulated thereby. The copper pattern portion covered with resist 14 is usually called an inner-layer pattern portion 16, which is generally higher by an amount corresponding to the thickness of the wiring pattern 13 as compared with the resist portion that is free of any copper pattern. In such a substrate structure, a substrate upper surface, before being coated with a resist film is as shown in FIG. 16. When an insulating film of resist 14 is applied to the substrate upper surface in this state, the substrate upper surface assumes an upper surface state as shown in FIG. 17 and sectional states as shown in FIGS. 11(a) to 18(c). Further, after being printed with creamy solder, the substrate upper surface assumes an upper surface state as shown in FIG. 19 and sectional states as shown in FIGS. 18(a) to 18(c).

Figure 24B:
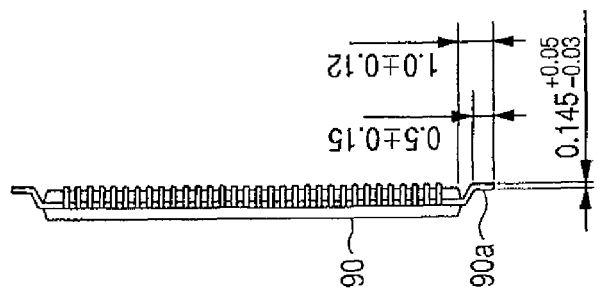
FIG. 24(b) is a side view and FIG. to 24(c) is a front view, which show the appearance and profile dimensions of a QFP as a mounted part.
Figure 24A:
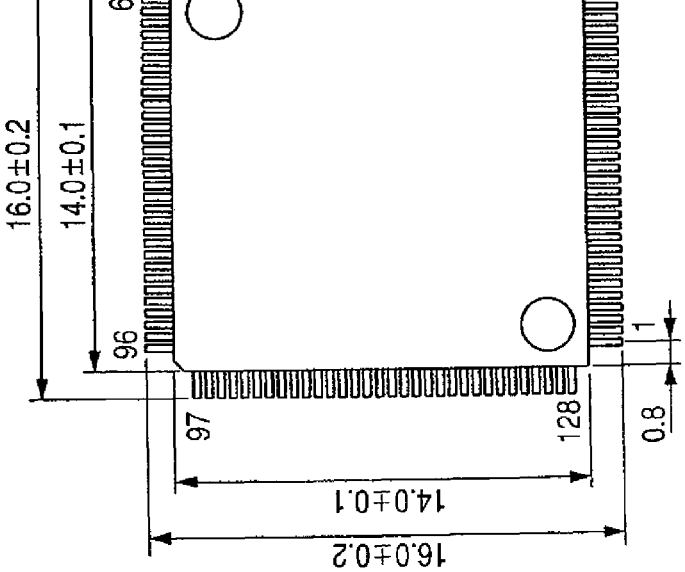
FIG. 24(a) is a top plan view.
Figure 24C:
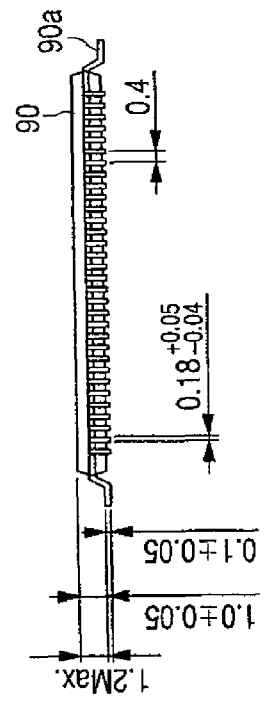

For example, plural pad portions 15 for mounting thereon a QFP 90, as shown in FIGS. 24(a) to 24(c), are formed centrally in FIG. 16, though the details will be described later in connection with FIGS. 25 and 26. Through holes 13a, are formed, which form a conductive path from the pad portions 15 to underlying wiring patterns, or back-side terminals through wiring patterns 13. Along the peripheral portion in FIG. 16, chip parts, such as chip resistors and chip capacitors, are formed, as well as pad portions 15, wiring patterns 13 and through holes 13a of various packages.

In state shown in FIG. 16, if an insulating film of resist 14 is applied, except for the pad portions 15 connected to terminals of circuit parts, the substrate upper surface is covered with the resist 14 in an exposed state of the pad portions 15, as shown in FIGS. 17 and 18(a) to 18(c). Further, if creamy solder is printed on the substrate, printed solder 10x comes to be present on the pad portions 15, as shown in FIGS. 19 and 20(a) to 20(c). In FIGS. 20(a) to 20(c), a height measurement reference plane 17 shown in FIG. 20(b), which will be described later, can be determined from the height measurement reference line 11a shown in FIG. 20(a) and the height measurement reference line 11b shown in FIG. 20(c).

In the above description of a principle of measuring the height and volume of printed solder and a positive method for measuring the height of the volume of printed solder, it has been made clear that the height of printed solder on the substrate can be measured. The measurement is made for each height measurement region 11. The height measurement region 11 is prepared automatically at the time of preparation of inspection data. Therefore, the height measurement reference lines 11a and 11b are also defined automatically.

As shown in FIG. 12, by measuring the height of the substrate upper surface on the height measurement reference lines 11a and 11b, it is possible to determine the height measurement reference plane 17. The height of printed solder printed on each pad portion 15 on the substrate base material 12 is measured on the basis of the height measurement reference plane 17. In this connection, consideration is here given to making a similar measurement with use of a raw substrate. Since the raw substrate is a substrate on which creamy solder is not printed, it is pad upper surface heights 18a, 18b, and 18c, based on the height measurement reference plane 17, that are obtained in an attempt to measure the height of the printed solder portion.

The pad upper surface heights 18a, 18b, and 18c are measured beforehand by measuring the raw substrate and are stored pad by pad. In accordance with the foregoing principle of measuring the height and volume of printed solder and positive method for detecting a height measurement reference in the measurement of height and volume of printed solder, the height of printed solder is measured pad by pad and the pad upper surface height which has been stored pad by pad is subtracted from the result of the measurement. As a result, the height of printed solder assumes a value measured on the basis of the pad upper surface.

For example, in the example of FIG. 12, the height measurement reference line 11a becomes an upper surface of resist 13 free of wiring patterns on the substrate base material 12, while the height measurement reference line 11b becomes an upper surface of resist 13 having wiring patterns on the substrate base material 12, and a plane including these upper surfaces is set as the height measurement reference plane 17. In the height measurement reference plane 17, the height measurement reference line 11b is greater by an amount corresponding to the thickness of the wiring patterns 13, so that the values of the pad upper surface height become larger in the order of pad upper surface height 18a of pad 15a→pad upper surface height of pad 18b of pad 15b→pad upper surface height 18c of pad 15c. Thus, the value subtracted by the measurement based on the pad upper surface is a value meeting the relation of pad 15a<pad 15b<pad 15c.

Thus, by measuring a raw substrate at the final stage of inspection data preparation and by measuring and storing the height data of each of the pads 15a, 15b, and 15c relative to the height measurement reference plane 17 produced automatically, the printed solder height measurement based on the pad upper surface can be conducted more accurately than the measurement based on the upper surface of the substrate 10 as an object of measurement. In this printed solder height measurement based on the pad upper surface, the flow of an inspection data preparing process using an inspection data preparing program 84 will be described below with reference to FIG. 15.

In S8401, a worker is requested to input, to the inspection system, gerber data of the metal mask used in printing. This is because the solder printing work involves the transfer of creamy solder onto a substrate through apertures of the metal mask; and, therefore, the shape, area and position of the transferred creamy solder can be detected by reading gerber data as metal mask design data.

In S8402, the worker is requested to designate the thickness of the metal mask. It is only the shape, area and position of the transferred creamy solder that can be obtained from the gerber data of the metal mask. Information on print height and the volume of printed solder is not included therein. Since the height of the creamy solder that is transferred onto the substrate depends on the thickness of the metal mask, it is possible to acquire information on a reference print height. Further, a reference volume can also be obtained by multiplying the reference area value obtained from gerber data by the mask thickness.

In S8403, the worker is requested to input determination values (parameters, upper- and lower-limit values) for determining whether the value obtained is acceptable or not. This is because the system in question is an inspection system; and, therefore, a value obtained by measurement must be determined whether falling under the range of a good product or not. Both upper- and lower-limit values are used for determining whether the measured value is acceptable or not. Therefore, the worker is requested to designate these values in the form of a percentage of the reference values. Since such percentage-designated upper- and lower-limit values are seldom changed depending on the object of measurement, inputted values are stored to lighten the worker's burden in the next and subsequent data preparing works.

In S8404, data conversion is performed when the above-stated conditions are satisfied to generate pad data 81 necessary for solder print inspection. A basic structure of the pad data 81 is as shown in FIG. 13. In this data conversion, inspection data (pad data) composed of pad XY coordinates 8102, pad XY width 8103, reference area 8104, reference volume 8105, and a determination value 8106, can be obtained by a number corresponding to the number of pads (the number of apertures). Pad number 8101 is a number assigned for the convenience of identifying pads by the inspection system in the interior of the same system. The pad number starts with No. 1, followed by serial numbers.

Inspection item 8107 is an identification flag for distinguishing whether 2D inspection is to be conducted as the pad inspection, or whether both 2D inspection and 3D inspection are to be conducted. Just after the data conversion, the inspection items remain vacant because there is no designated information. The height 8108 (an upper surface height 18a, 18b, 18c, . . . of each pad from the height measurement reference plane 17) from the reference plane, which is necessary for measuring the height of the printed solder on the basis of the pad upper surface, cannot be acquired from the above work and therefore remains vacant.

In S8405, the worker is requested to designate an inspection item pad by pad. All aperture information can be obtained by data conversion (S8404) and can be displayed graphically on the display unit 74. The worker is requested to designate a pad for 3D inspection by dragging a cursor with a mouse on the graphic image. As to the pad thus designated for 3D inspection, Flag which indicates the necessity of 3D inspection is added to inspection item 8107.

In S8406, field allocation is executed. Also, in 3D inspection there is a concept of the height measurement region 11 equal to the concept of field, and, hence, the inspection must be executed field by field. Therefore, the work for collecting random pads field by field is needed. This is called field allocation. First, for the pad for which 3D inspection is also required, field allocation is executed using the height measurement region 11 as a field. Thereafter, field allocation is executed for all of the pads, using the image pickup range 40 for 2D inspection as a field. As a result, field allocation data 82 is produced. A basic structure of the field allocation data is as shown in FIG. 14. All of the pad data which require 3D inspection are arranged before the pad data for 2D inspection.

The field allocation data 82 is made up of field No. 821, inspection item 822, central XY coordinates 823, start XY coordinates 824, end XY coordinates 825, field X size 826, field Y size 827, and pad No. 828. With the information of inspection item 8107 of the pad data 81, the inspection item 822 can determine whether it is 3D inspection or 2D inspection that is to be executed. The central XY coordinates 823 indicate coordinates of the field center. In 2D inspection, a robot is controlled on the basis of this coordinate value in such a manner that the center of the camera field coincides with the coordinates concerned. The start XY coordinates 824 and the end XY coordinates 825 represent field scan start coordinates and end coordinates, respectively, of the height measurement region 11 in 3D inspection. The field X size 826 and the field Y size 827 represent field sizes. Correlation with the information of pad data 81 shown in FIG. 13 can be effected by the pad number recorded in the pad No. 828.

In S8407, a raw substrate is set to the inspection system. On the basis of the field allocation data 82 and the pad data 81, the substrate is moved to the position for imaging the first field (height measurement region 11) in 3D inspection. Then, as noted earlier, the first 1024 sheets of picked-up image data 53 for 3D inspection are obtained.

In S8408, the substrate heights on the height measurement reference lines 11a and 11b are measured from the first and 1024th sheets of image data.

In S8409, the height measurement reference plane 17 shown in FIG. 12 is produced from the substrate heights on the height measurement reference lines 11a and 11b.

In S8410, the height of a pad upper surface within the field (height measurement region 11) is measured. The pad to be measured can be checked by making reference to both field allocation data 82 shown in FIG. 14 and the pad data 81 shown in FIG. 13.

In S8411, data of the thus-measured heights 18a, 18b, 18c, . . . of the pad upper surfaces, based on the height measurement reference plane 17, are stored by pad in the region of height 8108 from the reference plane of pad data 81 shown in FIG. 13.

The above-described processings from S8406 to S8411 are executed repeatedly until completion is achieved for all of the fields. When the above-described processings are completed, the height of an upper surface of each pad relative to the original height measurement reference plane produced automatically by the inspection system is defined. Thus, the data necessary for measuring the pad upper surface reference can be produced almost automatically.

Figure 21:
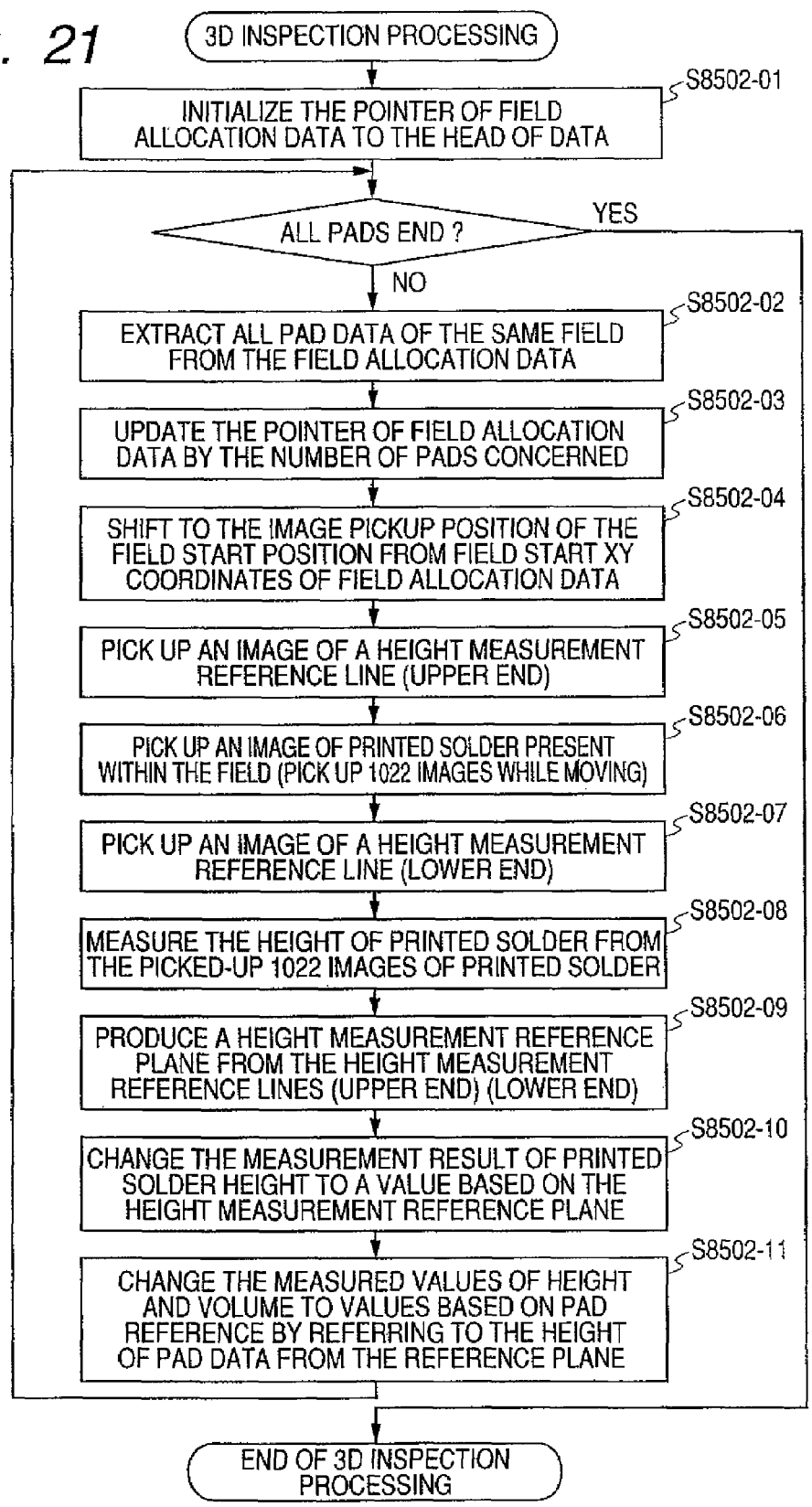
FIG. 21 is a flow chart showing a 3D inspection procedure.

Next, with reference to FIG. 21, in addition to FIGS. 3 to 7 to which reference has been made above, a description will now be given concerning a method of inspecting the height and volume of printed solder based on a pad upper surface, while taking a measure against warping of a substrate in the 2D-3D solder print inspection system of this embodiment. FIG. 21 is a flow chart showing a processing procedure for 3D inspection.

With use of the inspection data prepared by the foregoing method for preparing inspection data for measuring the height and volume of printed solder based on a pad upper surface, it is possible to measure the height and volume of printed solder based on a pad upper surface while absorbing the warp condition of a substrate. This point will be described below with reference to FIG. 21. FIG. 21 illustrates in detail a "3D inspection" processing as a substrate inspection procedure shown in FIG. 22.

In S8502-01, a pointer for pointing data is moved (initialized) to the head of the field allocation data 82.

In S8502-02, all the pad data within one and the same field can be extracted by extracting data which are the same in the field center XY coordinates 823, field X size 826, and field Y size in the field allocation data 82.

In S8502-03, the pointer position is updated by an amount corresponding to the number of pads to be measured so as to indicate the head of a pad data group in the next field.

In S8502-04, the X-axis robot 71 and the Y-axis robot 72 are operated on the basis of the field start XY coordinates 84 in the field allocation data 82 to provide a positional relation in which the height measurement reference line 11a in the height measurement region 11 is imaged centrally of the camera 31.

In S8502-05, first, for permitting the warp condition of the substrate 10 to serve as an object of measurement, as shown in FIG. 6, the image size of the picked-up image data 53 for 3D inspection is set to about 1024 pixels×256 pixels to obtain picked-up image data 53a for the measurement of substrate height. Since the resolution is 20 μm, the image pickup range 41 for 3D inspection becomes 20.48 mm×5.12 mm.

An image of an upper end portion of the height measurement region 11 is picked up in this image pickup range of the picked-up image data 53a for substrate height measurement. Since a substrate upper surface is to be detected here, the exposure time is set at 5 ms so that there is obtained a slit light trace 531 that is bright enough to permit detection of a slit light trace on the substrate, as shown in FIG. 3. Under this condition, the slit light trace 531 on the substrate can be imaged at an appropriate lightness and width. Under this image pickup condition, the slit light trace 532 on printed solder assumes a state of overexposure, so that an image is picked up at a saturated lightness and a thickened width.

Thus, the two height information pieces, which are represented by the substrate surface and the upper surface of printed solder, are mixed together. However, since it is evident that the substrate upper surface is the lower surface, a substrate upper surface height position (on-substrate slit light trace 532) on the height measurement reference line 11a can be specified easily.

In S8502-06, first, picked-up image data 53b for the measurement of printed solder height is defined. As shown in FIG. 7, the image size is set at 1024 pixels×32 pixels. Since the resolution is 20 μm, the image pickup range 41 for 3D inspection becomes 20.48 mm×0.64 mm. Further, as shown in the same figure, a measurement reference line 533 is set at the position of the twelfth pixel from below of the picked-up image data 53b.

The picked-up image data 53b for measuring the height of printed solder is set onto the image pickup element of the camera in such a manner that the measurement reference line 533 is aligned with the substrate upper surface height position (531) on the height measurement reference line 11a. A normal height of printed solder is 0.16 mm, which corresponds to eight pixels on the picked-up image data 53b. Therefore, a positional relation between the slit light trace 531 on the substrate and the slit light trace 532 on printed solder has a positional relation as shown in FIG. 7, referred to previously.

With the picked-up image data 53b, 1022 sheets of images for detecting an upper surface of printed solder are picked up while setting the exposure time at 0.05 ms. At such a short exposure time, only the slit light trace 532 on printed solder is imaged on the picked-up image data, while the slit light trace 531 on the substrate is not imaged on those data.

In S8502-07, the last 1024th image is picked up at a longer exposure time of 5 ms. Since the exposure time is set longer, it is possible to specify the substrate upper surface height position (slit light trace 531 on the substrate) on the height measurement reference line 11b.

In S8502-08, the foregoing processing of the principle of measuring the height and volume of printed solder is performed for the second to 1023th sheets of picked-up image data 53b for measuring the height of printed solder, whereby it is possible to measure the height of printed solder based on the measurement reference line 533.

In S8502-09, since the substrate upper surface height on the height measurement reference line 11a and that on the height measurement reference line 11b are measured with use of the first sheet of picked-up image, it is possible to detect an upper surface of the substrate (substrate warp, which, within this limited region, can be considered to be a substrate inclination) in the height measurement region 11.

In S8502-10, the height measurement result of printed solder is re-evaluated on the basis of the detected substrate upper surface, whereby a printed solder height measurement result is obtained based on the substrate upper surface that is not influenced by the warp condition of the substrate.

In S8502-11, by making reference to the data of the height 8108 from the reference plane of pad data 81 up to the pad upper surface and by adding the data to the printed solder measurement result, it is possible to change the measurement result into a pad upper surface reference.

The above-described processing is repeated until it is completed for all of the pad data in the field allocation data 82.

Figure 22:
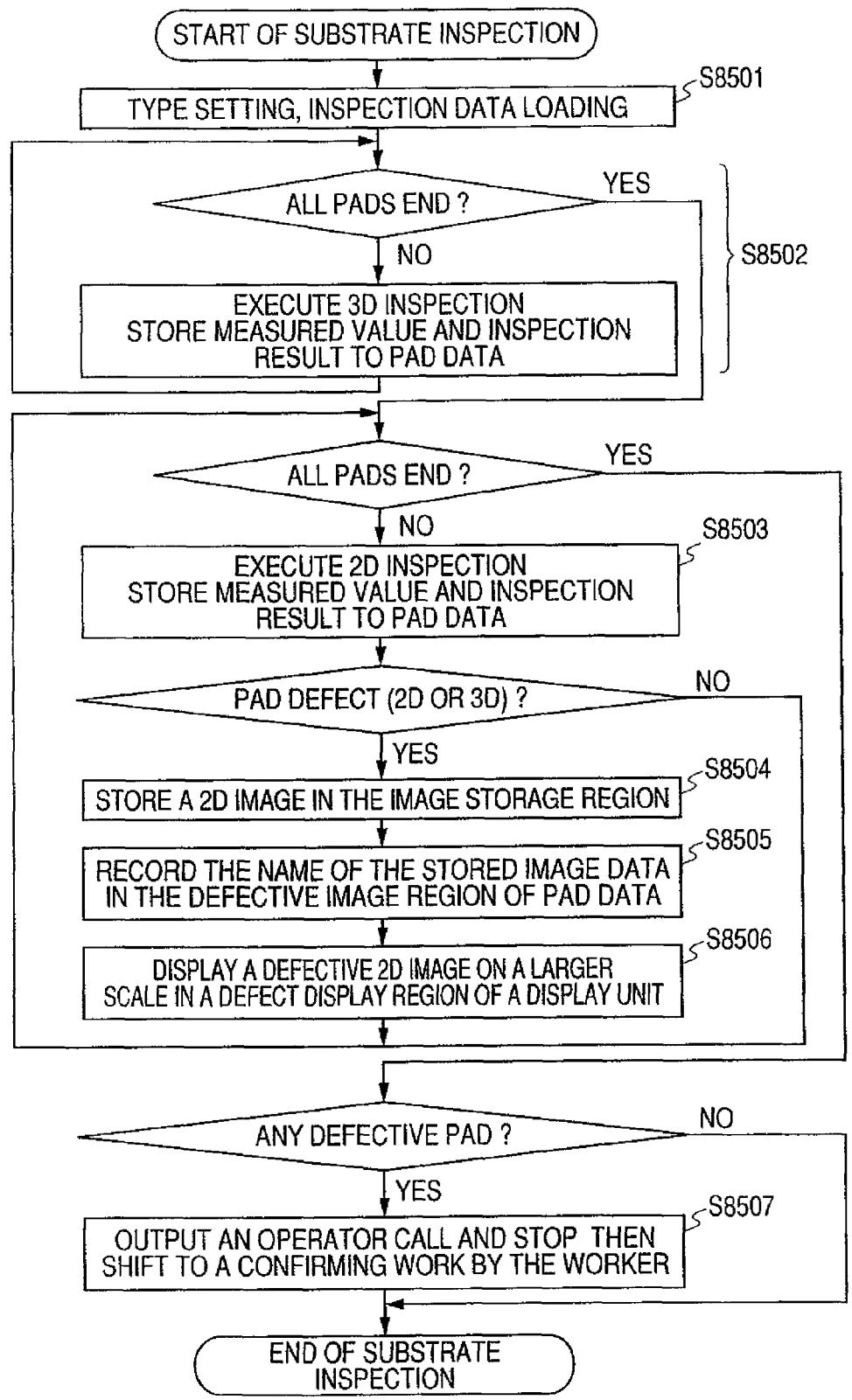
FIG. 22 is a flow chart showing a substrate inspection procedure.
Figure 23:
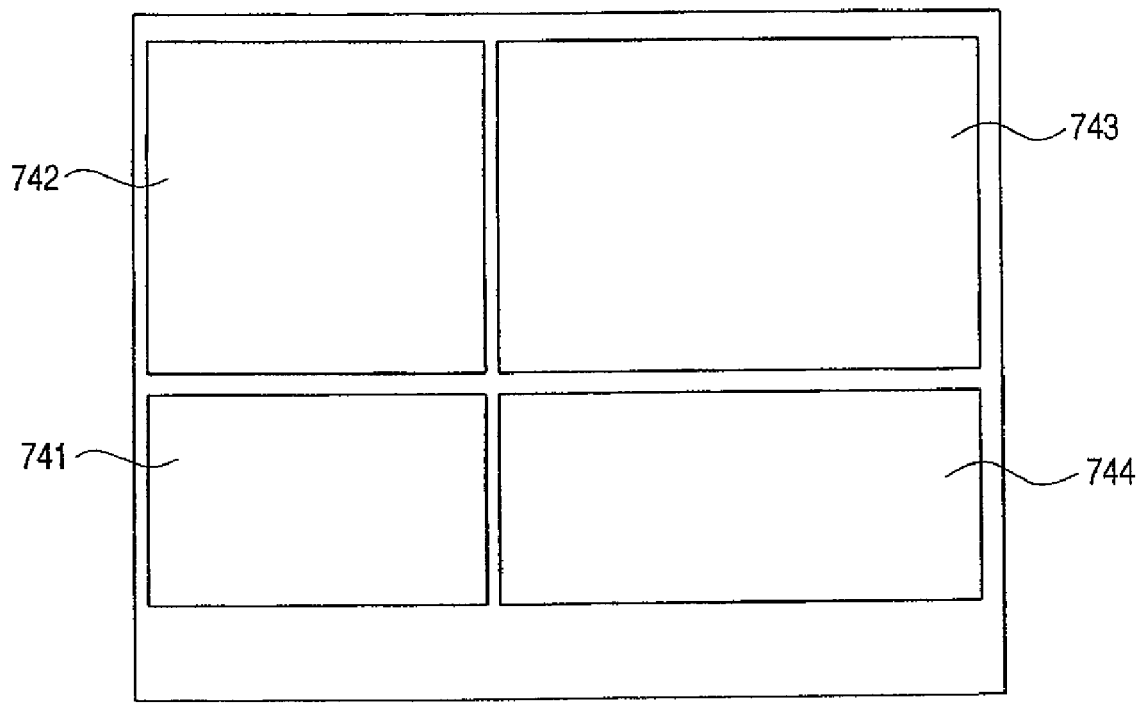
FIG. 23 is a diagram which shows a display position of enlarged images of defective portions on a display screen of a display unit used in the inspection system.

Next, with reference to FIGS. 22 and 23, in addition to FIGS. 1, 2, 13, and 14 to which reference has been made above, a description will be given of an example of a 3D solder print inspection method suitable for visual determination in the 2D-3D solder print inspection system of this embodiment. FIG. 22 is a flow chart showing a substrate inspection procedure, and FIG. 23 shows a display position of enlarged images of defective portions on a display screen of a display unit used in the inspection system.

The construction of the inspection system using this 3D solder print inspection method suitable for visual determination is as shown in FIG. 1. A reddish green LED lighting unit 21 and a bluish LED lighting unit 22 to be used for 2D inspection, as well as a slit lighting unit 23 to be used for 3D inspection, are mounted so that they can be turned ON and OFF freely in accordance with commands given from the overall control section 80. There is also a camera 31 for picking up images on the substrate. The camera 31 is a CMOS area camera. In this area camera, as shown in FIG. 2, the image pickup range can be switched to the image pickup range 40 for 2D inspection and to the image pickup range 41 for 3D inspection selectively.

Thus, although it is only one camera 31 that is mounted, both 2D inspection and 3D inspection can be performed by a single camera, as is apparent from the above description.

Next, with reference to the flow chart of FIG. 22 using the inspection execution program 85, the following description is provided concerning the implementation of a function unique to the 3D inspection system, which also possesses the 2D inspection function.

In S8501, a large number of substrate inspection data are recorded in the inspection system. In accordance with a command given by the worker, type setting and inspection data for the substrate about to be inspected are called from among the inspection data on the substrate, and this data is loaded to the execution region, i.e., the pad data 81 and the field allocation data 82.

In S8502, first, 3D inspection is performed on the basis of the field allocation data 82. From the start XY coordinates 824 and the end XY coordinates 825 in the field allocation data 82 shown in FIG. 14, scanning is performed within the height measurement region 11 to obtain picked-up image data 53 for 3D inspection. A 3D measurement is performed from the image data. Pads within one and the same field are specified from the information described in field No. 821 and pad No. 828 in the field allocation data 82, and a 3D measurement is performed pad by pad. By adding the height 8108 from the reference plane of the pad data 81 to the result of the measurement, a measurement result is obtained, based on a pad upper surface. The measurement value and measurement result are recorded in the measured value 8109 and 3D determination result 8111 of the pad data 81 shown in FIG. 13.

In S5503, when all of the 3D inspection is over, 2D inspection is performed on the basis of the field allocation data 82 and the pad data 81. The measured value and determination result for each pad are recorded in the measured value 8109 and 2D determination result 8110 of the pad data 81. Though not shown in the drawings, the measured value 8109 has a region capable of recording 3D and 2D measured values independently.

In S8504, as to pads found to be defective in the 2D inspection or 3D inspection, the corresponding 2D picked-up images are recorded together with the file name in the picked-up data storage region 83.

In S8505, the file name of the thus-stored 2D picked-up image data is recorded in the defective image 8112 of pad data 81.

In S8506, as to the pads found to be defective in 2D inspection or 3D inspection, as shown in FIG. 23, their 2D picked-up images are displayed on a larger scale in a defective pad enlarged display region 741 of the display unit 74. The above-described processings from S8502 to S8506 are repeated until the end of the inspection for all of the pads.

In S8507, in the event there should be even one defective pad at the end of both 3D inspection and 2D inspection, an operator call is outputted to stop the operation. Upon issuance of such an operator call, the worker is requested to visually check the pad (printed solder) which has been determined to be defective by the inspection system. This visual confirmation is performed while looking at the 2D picked-up image displayed on a larger scale on the defective pad enlarged display region 741 of the display unit 74. This image has been picked up by the camera 31 of a black-and-white area type through the lens 32. The worker can give a proper acceptance-or-not judgment in the manner of checking an enlarged microscopic image.

In the display unit 74 shown in FIG. 23, the defective pad enlarged display region 741 has a format permitting the simultaneous display of defective images at eight places. When more than eight defects occur, nine and subsequent defective images can be displayed by operating a scroll bar (not shown) which lies on the right-hand side of the defective pad enlarged display region 741.

In this example, although an operator call is issued in the presence of even one defective pad, a versatile setting may be made such as, for example, an operator call is not outputted when the number of minor defects is less than a predetermined number. In FIG. 23, the numeral 742 denotes a camera picked-up image region, numeral 743 denotes a defective pad display region, showing an overall substrate image, and numeral 744 denotes an inspection counter and various information display regions.

Next, with reference to FIGS. 24(*a*) to 29(*c*) in addition to FIGS. 16 to 20(*c*) to which reference has been made above, a description will be given below about the necessity and usefulness of a partial 3D inspection in the 2D-3D solder print inspection system of this embodiment. FIGS. 24(*a*) to 24(*c*) show the appearance and profile dimensions of a QFP as a mounted part, FIG. 25 schematically shows a mounted state of the QFP onto a creamy solder printed substrate, FIG. 26 shows a B-B' section in FIG. 25, FIG. 27 shows print patterns of a substrate for an actual portable telephone, FIGS. 28(*a*) to 28(*c*) show the appearance and profile dimensions of a BGA (CSP) as a mounted part, and FIGS. 29(*a*) to 29(*c*) show the appearance and profile dimensions of a connector as a mounted part.

The structure of the substrate is as shown in FIGS. 16 to 20(*c*). According to a commonly-used substrate structure, as shown in FIG. 16, wiring patterns 13 are formed of copper or the like on the substrate base material 12, which is formed using a glass fabric-based epoxy resin. With the wiring patterns 13 as they are, a problem will occur, such as a short-circuit, upon deposition of electrically conductive foreign matter or the like on the wiring patterns. Therefore, the resist 14, which serves as an insulating film, is applied onto the substrate, except for the portions to be connected to terminals of a circuit part.

In the substrate thus formed, as shown in FIG. 17 and FIGS. 18(*a*) to 18(*c*), the portions for connection with terminals of a circuit component are free of the resist 14 and assume a partially exposed form of copper wires. The portions in question correspond to pad portions 15. As shown in FIG. 19 and FIG. 20(*a*) to 10(*c*), creamy solder is printed on the substrate, with the result that printed solder 10*x* is formed by transfer onto the pad portions 15 with a certain thickness and shape.

Positioning is performed until coincidence of the pad portions 15 is achieved on the substrate with terminals of the circuit part, and, thereafter, the circuit part is mounted onto the substrate with printed solder 10*x* formed thereon by transfer. Reference is here made to a QFP (Quad Flat Package) which is a typical circuit part. The QFP, indicated at 90, has an appearance and profile dimensions as shown in FIGS. 24(*a*) to (*c*). FIGS. 25 and 26 show a mounted state of the QFP 90 on the substrate after transfer thereto of the printed solder 10*x*.

Figure 25:
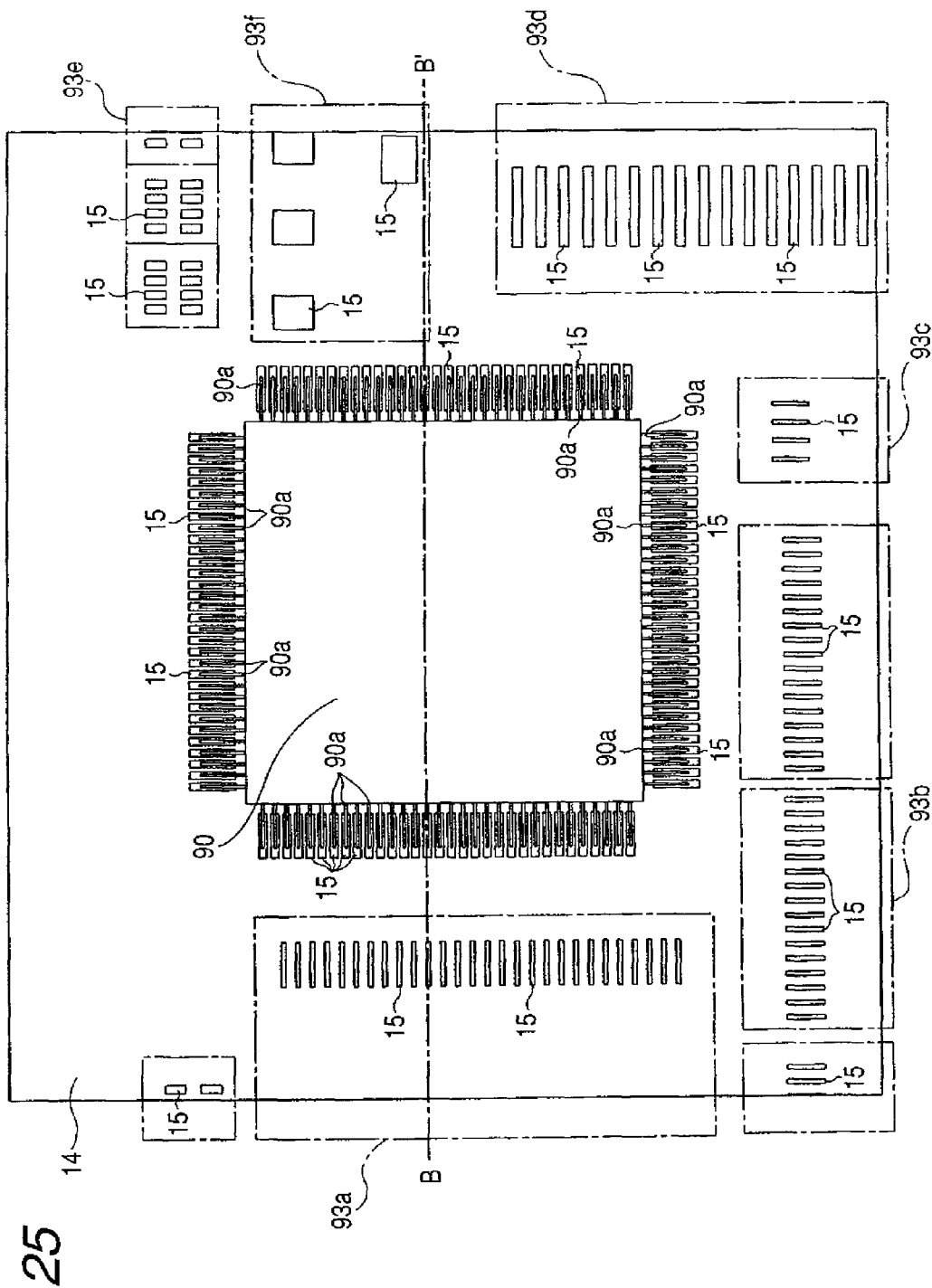
FIG. 25 is a top plan view that schematically shows a state of the QFP that has been mounted onto a creamy solder printed substrate.
Figure 26:
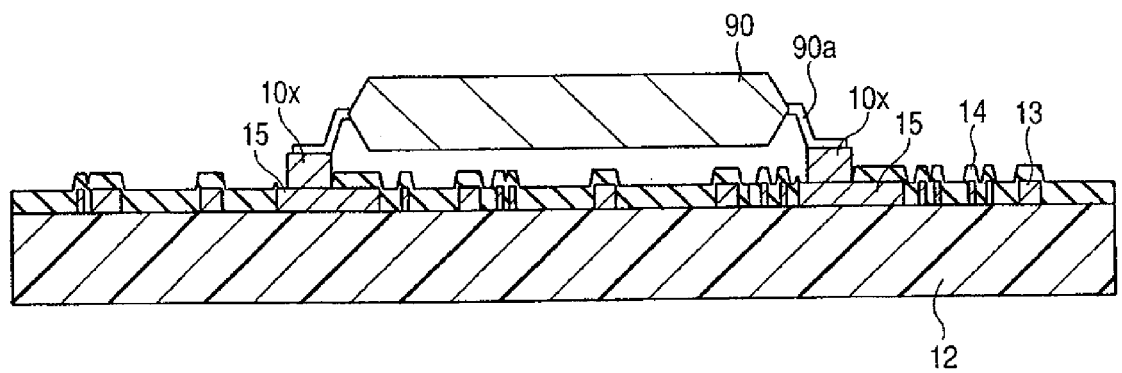
FIG. 26 is a section view taken along line a B-B' in FIG. 25.
Figure 27:
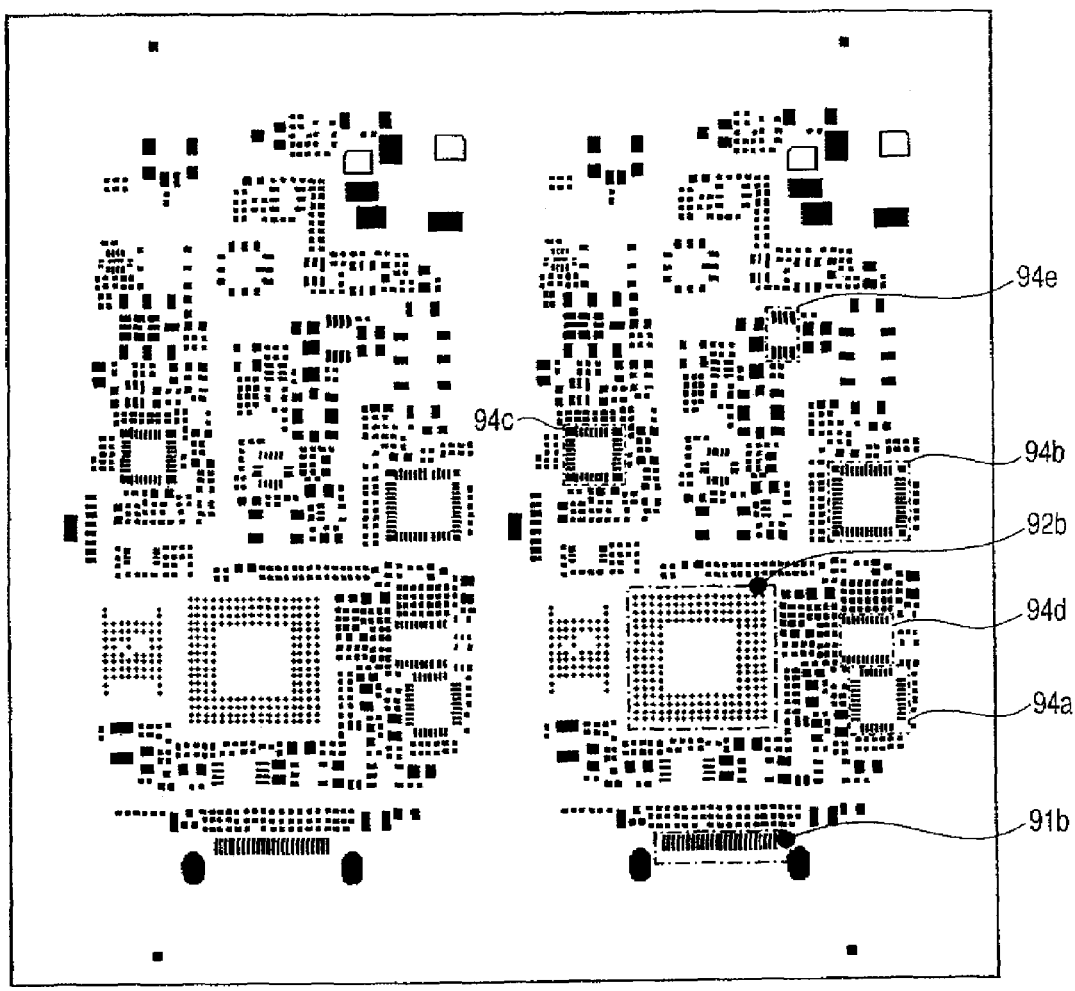
FIG. 27 is a diagram which shows print patterns of a substrate for an actual portable telephone.

In the state shown in FIGS. 25 and 26, the QFP 90 alone is mounted on the substrate and terminals 90*a* thereof are connected to the pad portions 15 through the printed solder 10*x*. Actually, various SOPs (Small Outline Packages) having plural terminals are mounted also on peripheral areas 93*a*, 93*b*, 93*c*, 93*d*, and 93*e*, and chip parts, such as a chip resistor and a chip capacitor, are mounted as circuit parts on an area 93*f*.

By subsequent passing of the assembly through a reflow furnace, the printed solder 10*x* melts and the pad portions 15 on the substrate and the terminals of the circuit part are brought into a mutually connected state electrically. Further, after subsequent passing of the assembly through a cooling step, the shape of the solder at room temperature becomes fixed, and, thus, the substrate assembly is completed. Since the substrate assembling work is performed in accordance with such a process, the print quality of the printed solder 10*x* in creamy solder printing greatly influences the solder connectability after the reflow.

By passing through the reflow furnace, the printed solder 10*x* becomes liquid and retains a surface tension. Therefore, even if the print shape is somewhat disordered or somewhat dislocated, the position of the liquid printed solder 10*x* converges to an appropriate position under what is called a self-alignment effect. Accordingly, as noted earlier, what is more important is the amount (volume) of the printed solder 10*x*. This is due to the following reason. If the amount of the printed solder 10*x* is small, a sufficiently high strength bonding is not ensured between the terminals of the circuit part and the substrate pad portions 15. On the other hand, too much of an amount thereof is likely to cause a short-circuit between adjacent pads and terminals.

In normal solder printing, there is a correlation between the amount of solder and the 2D shape thereof. However, in recent high density packaged substrates, there are print patterns for which the correlation may not be ensured. Since the printed solder 10*x* is formed through the process of transferring creamy solder to the substrate through apertures of a metal mask, it can be easily presumed that the applicability of creamy solder will be deteriorated as the aperture diameter becomes smaller.

Figure 28B:
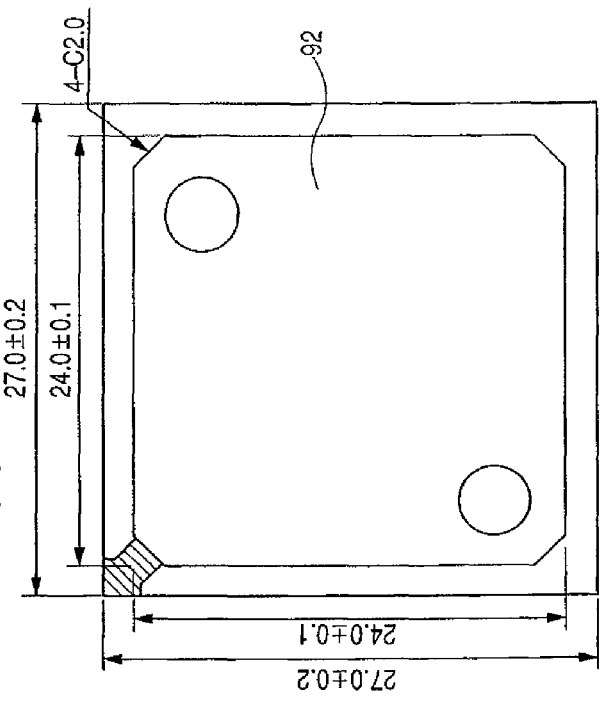
FIG. 28(b) is a plan view and FIG. 28(c) is a first view, which show the appearance and profile dimensions of a BGA (CSP) as a mounted part.
Figure 28C:
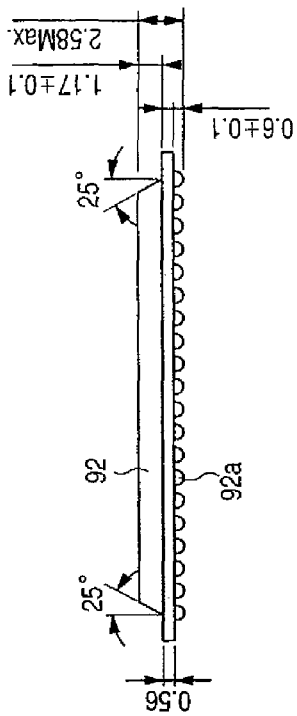
Figure 28A:
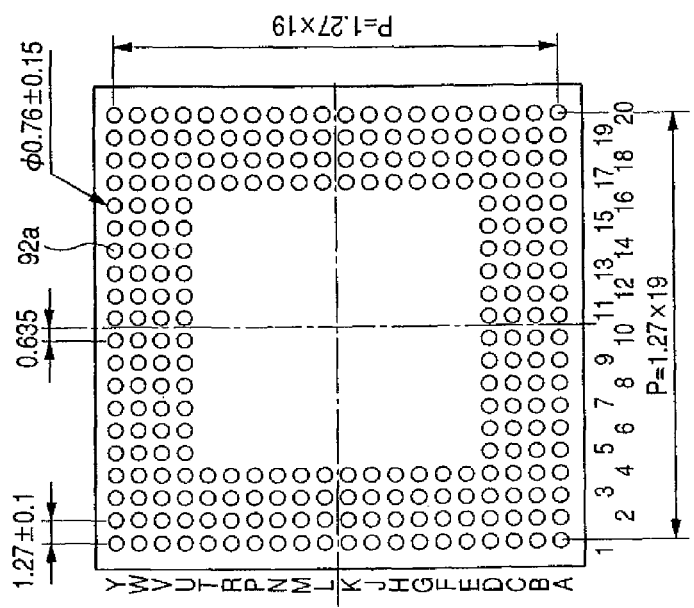
FIG. 28(a) is a bottom view.
Figure 29A:
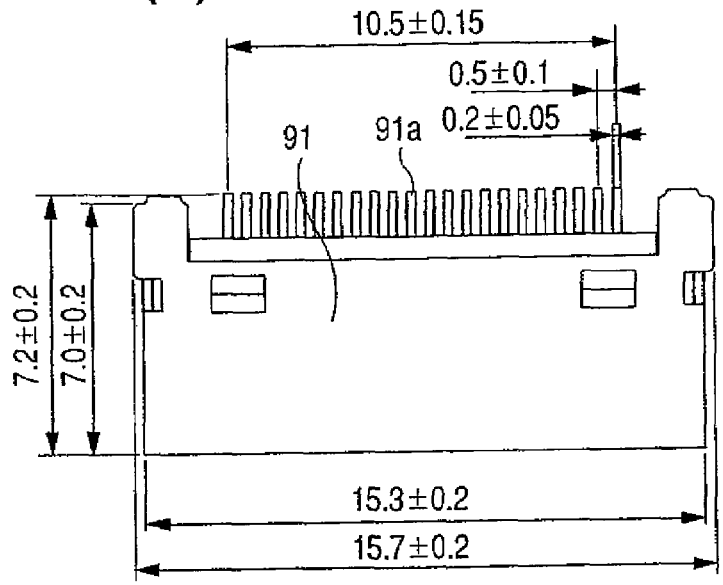
FIG. 29(a) is a plan view.
Figure 29B:
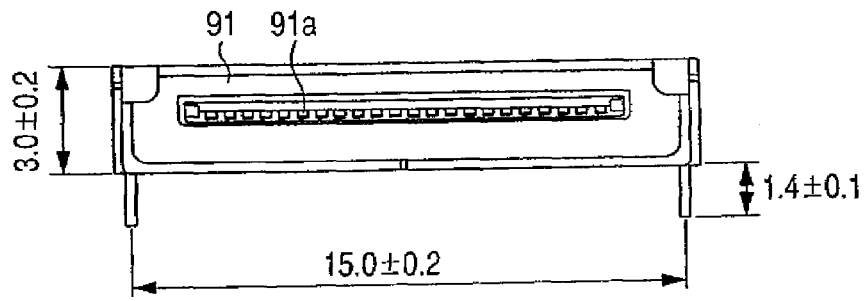
FIG. 29(b) is a front view and FIG. 29(c) is a side view, which show the appearance and profile dimensions of a connector as a mounted part.
Figure 29C:
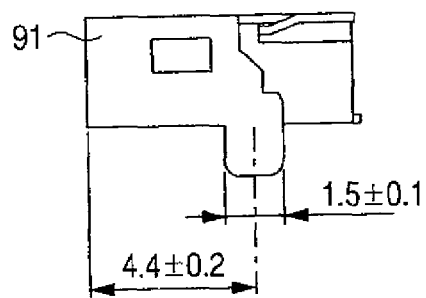

Actually, on a substrate for a portable telephone such as shown in FIG. 27, which is one of the leading-edge products of high density packaging, there are a BGA (Ball Grid Array: CSP (Chip Size Package) 92 as shown in FIGS. 28(*a*) to 28(*c*) and a connector 91 as shown in FIGS. 29(*a*) to 29(*c*), which is to be used for connection with an external device or for electric charging. As other main mounted parts, a QFP having plural terminals as mentioned above is mounted on mounting portions 94*a*, 94*b*, and 94*c*, while an SOP having plural terminals is mounted on mounting portions 94*d* and 94*e*. Various circuit parts, including chip parts, are also provided.

The substrate for a portable telephone as shown in FIG. 27 is an example of a dividable substrate configuration (a configuration permitting the provision of plural substrates by dividing a single substrate) which can be divided into two right and left substrates of the same structure. In each of the divided substrates, terminals (bumps) 92*a* of the BGA (CSP) shown in FIG. 28 are mounted on a BGA (CSP) mounting portion 92*b* (pad portion: black portion), while terminals 91*a* of the connector 91 shown in FIG. 29 are mounted on a connector mounting portion 91*b*. In both circuit parts, after mounting, soldered portions are sandwiched in between the parts and the substrate and cannot be confirmed visually. Therefore, a guaranteed quality of the printed solder 10*x* just after the transfer thereof is important. Besides, since the pad portions of these parts are small in pattern size as compared with other parts, it cannot be said that the applicability of the solder is good. Thus, the solder print inspection for these parts is more important.

Since the pad portions of the BGA (CSP) 92 are circular in aperture diameter, a relatively good applicability of solder can be ensured for their small size. However, the pad portions of the connector 91 are in a rectangular shape of a fairly large aspect ratio, so that printing at a uniform thickness becomes more difficult as the aperture size becomes smaller.

Therefore, as a method for inspecting the printed solder 10*x*, it is considered suitable, from the standpoint of quality-efficiency balance and for the purpose of preventing an erroneous setting for a printer, to perform 3D inspection of the BGA (CSP) mounting portion 92*b* which is poor in solder applicability and narrow in pitch and of the connector mounting portion 91*b* of a substrate for a portable telephone, for example, in addition to 3D inspection of the four corners and central portion of each substrate, and to guarantee the quality of the other portion by 2D inspection.

The following description is directed to modified and applied examples of the 2D-3D solder print inspection system according to this embodiment. In the above-described embodiment, although a single camera is used in common to both 2D inspection and 3D inspection, a camera for 2D inspection and a camera for 3D inspection may be used independently. Even in this case, the essence of the present invention does not change at all. Moreover, although an image obtained by the black-and-white area camera for 2D inspection is used for visual confirmation, a color camera may be adopted, whereby the visual confirmation performance is further improved. Further, not only in the image picked up by the camera for 2D inspection used, but also a color camera and a lighting unit dedicated to visual confirmation may be used to further improve the visual confirmation performance.

Figure 30:
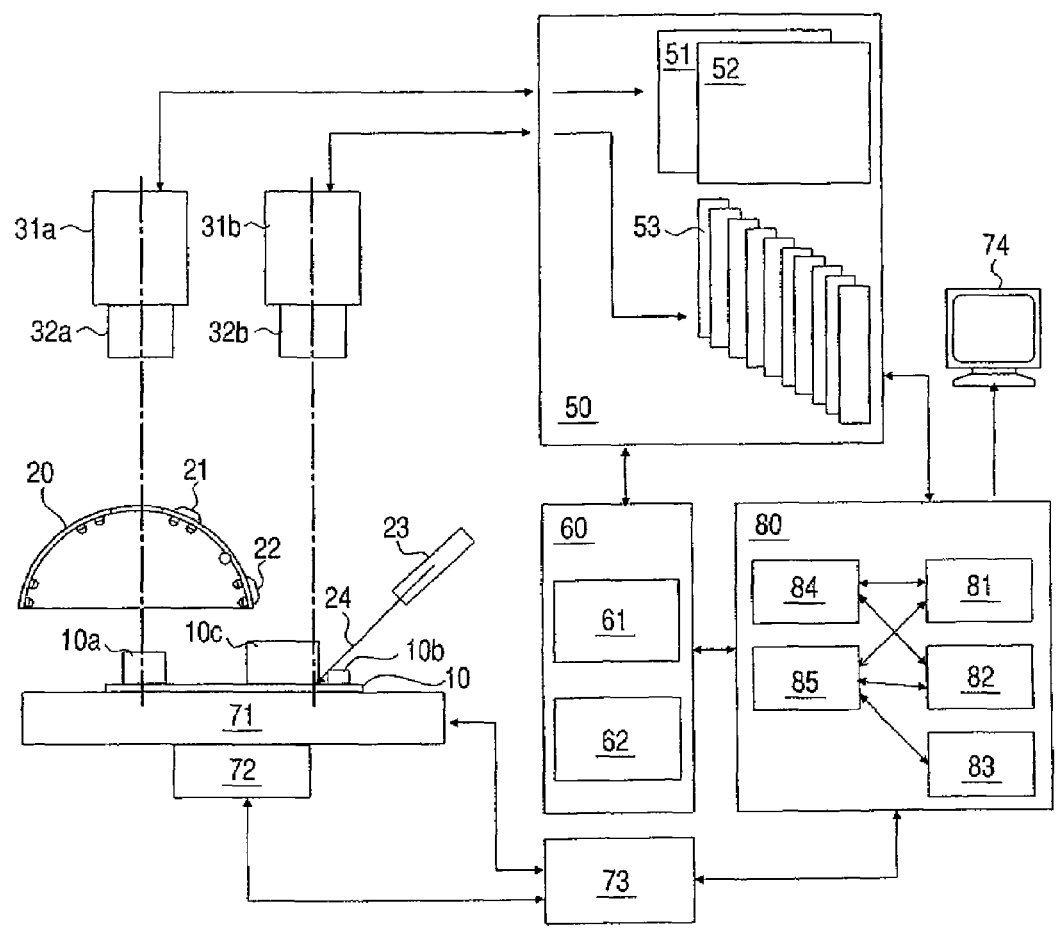
FIG. 30 is a diagram showing the overall configuration of a 2D-3D solder print inspection system (a twin-lens camera)
Figure 31A:
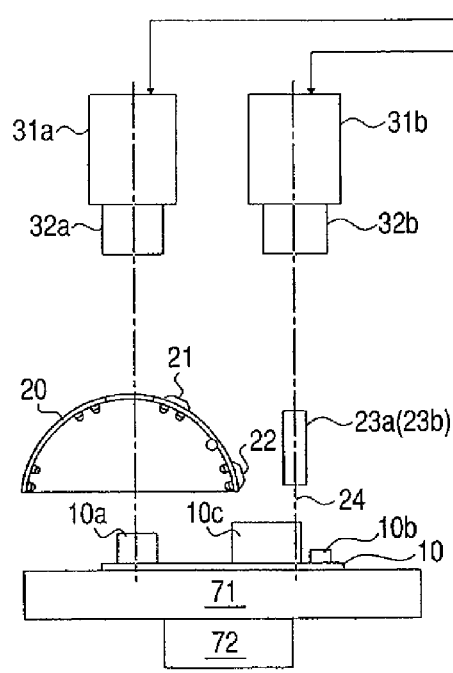
FIG. 31(a) is a front view and FIG. 31(b) is a side view showing the overall configuration of a 2D-3D solder print inspection system (a two-slit lighting device type)
Figure 31B:
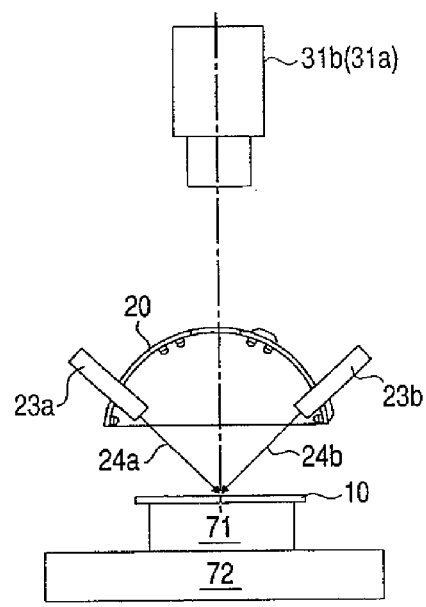
Figure 32:
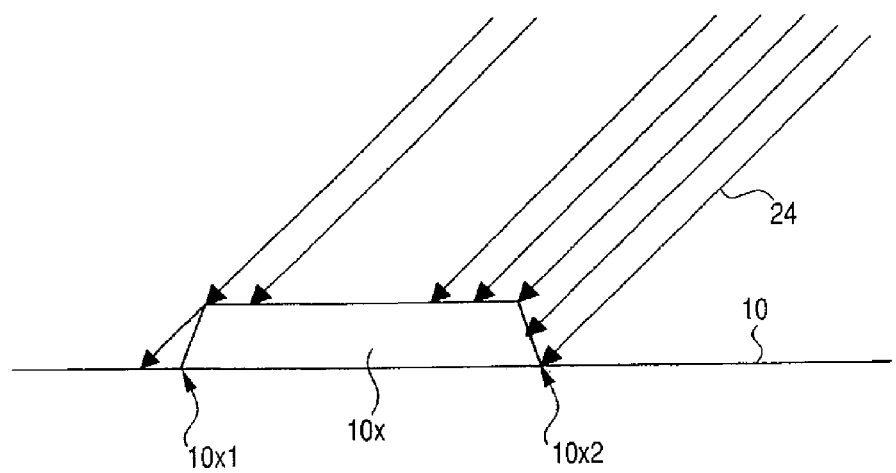
FIG. 32 is a diagram illustrating the presence of a surface whose height cannot be measured.

Now, with reference to FIGS. 30 to 32, a description will be given of a separate configuration having both a 2D inspection camera and a 3D inspection camera, and also a configuration of an inspection system wherein a region incapable of being measured is not generated. FIG. 30 is a diagram showing the overall configuration of a 2D-3D solder print inspection system (a twin-lens camera). FIGS. 31(*a*) and 31(*b*) are diagrams showing the 2D-3D solder print inspection system (a two-slit lighting unit type), and FIG. 32 is a diagram for explaining the presence of a surface whose height cannot be measured.

The configuration having both a 2D inspection camera and a 3D inspection camera is as follows. Basically, both 2D inspection and 3D inspection can be performed with a single camera. However, since a picked-up image in 2D inspection and that in 3D inspection are greatly different from each other, the performance required of the former and that required of the latter are also different inevitably. Thus, for using a single camera for both 2D and 3D inspections, the camera is required to exhibit a higher performance.

At present, a camera capable of implementing both 2D inspection and 3D inspection with a satisfactory performance is not available. A more realistic solution may be the provision of dedicated cameras, as shown in FIG. 30. In this example of a 2D-3D solder print inspection system (a twin-lens camera), a CCD camera (a camera using CCD as an image pickup element) 31*a*, which is advantageous in point of sensitivity, is used for 2D inspection, while a CMOS camera (a camera using CMOS transistor as an image pickup element) 31*b*, which is capable of making a partial read and having a high frame rate, is used for 3D inspection. It goes without saying that even if the camera for 2D inspection and the camera for 3D inspection are mounted independently, the essence of the present invention does not change at all and the functions of the constituent elements are the same as those shown in FIG. 1.

The inspection system configuration for not generating a region incapable of being measured is as follows. In the description of the foregoing embodiment, it has been indicated that the measurement of height can be carried out by radiating slit light 24 obliquely to the substrate 10 as an object of measurement that has been coated with printed solder 10*x*. However, as shown in FIG. 32, a side face 10*x*1 of the printed solder 10*x* on the side opposite to the slit lighting unit 23 is hidden from the slit light 24 and the height thereof cannot be measured.

The problem in which an inclined side face of the printed solder 10*x* cannot be measured is not so serious in the case where printed solder has a large upper surface area relative to the solder print height, but in the case of a very small printed solder area, the problem in question is not negligible, because it exerts a great influence on the measured volume. In recent high density packaged substrates, there is an increasing tendency of using a very small area of printed solder, and, therefore, it is necessary to solve the problem in question. For solving this problem, on the side opposite to a slit lighting unit 23*a*, there is disposed a slit lighting unit 23*b* of a similar structure, as shown in FIGS. 31(*a*) and 31(*b*).

In this example of the 2D-3D solder print inspection system (a two-slit lighting unit type), first only the slit lighting unit 23*a* is turned ON and the height of printed solder 10*x* (10*a*, 10*b*, 10*c*) printed on the substrate 10 as an object of measurement is measured in the manner described above, whereby height information can be obtained with respect to a portion other than the slant face positioned on the side opposite to the slit light unit 23*a*. Next, the slit lighting unit 23*a* is turned OFF, while the slit lighting unit 23*b* is turned ON, and the height of the printed solder 10*x* is measured in the manner described above, whereby height information can be obtained with respect to a portion other than the slant face positioned on the side opposite to the slit lighting unit 23*b*.

These two measurement results, when compared with each other, are almost equal to each other in that the height measurement could be effected. On the other hand, as to the side faces of the printed solder 10x, one of the two measurement results involves a measured value, while the other shows that the measurement was not feasible. Thus, different results are obtained.

To solve this problem, the two measurement results are compared with each other for each arbitrary point out of points which form the surface of the printed solder 10x, and as to a point having measured values in both measurement results, a mean value of the two measured values is regarded as a measured value of the height of that point. On the other hand, as to a point having a measured value in one measurement result and not having a measured value in the other measurement result, the one measured value is regarded as a measured value of that point. By performing such processing, it is possible to realize a 3D measurement that is free of a dead angle.

Figure 33:
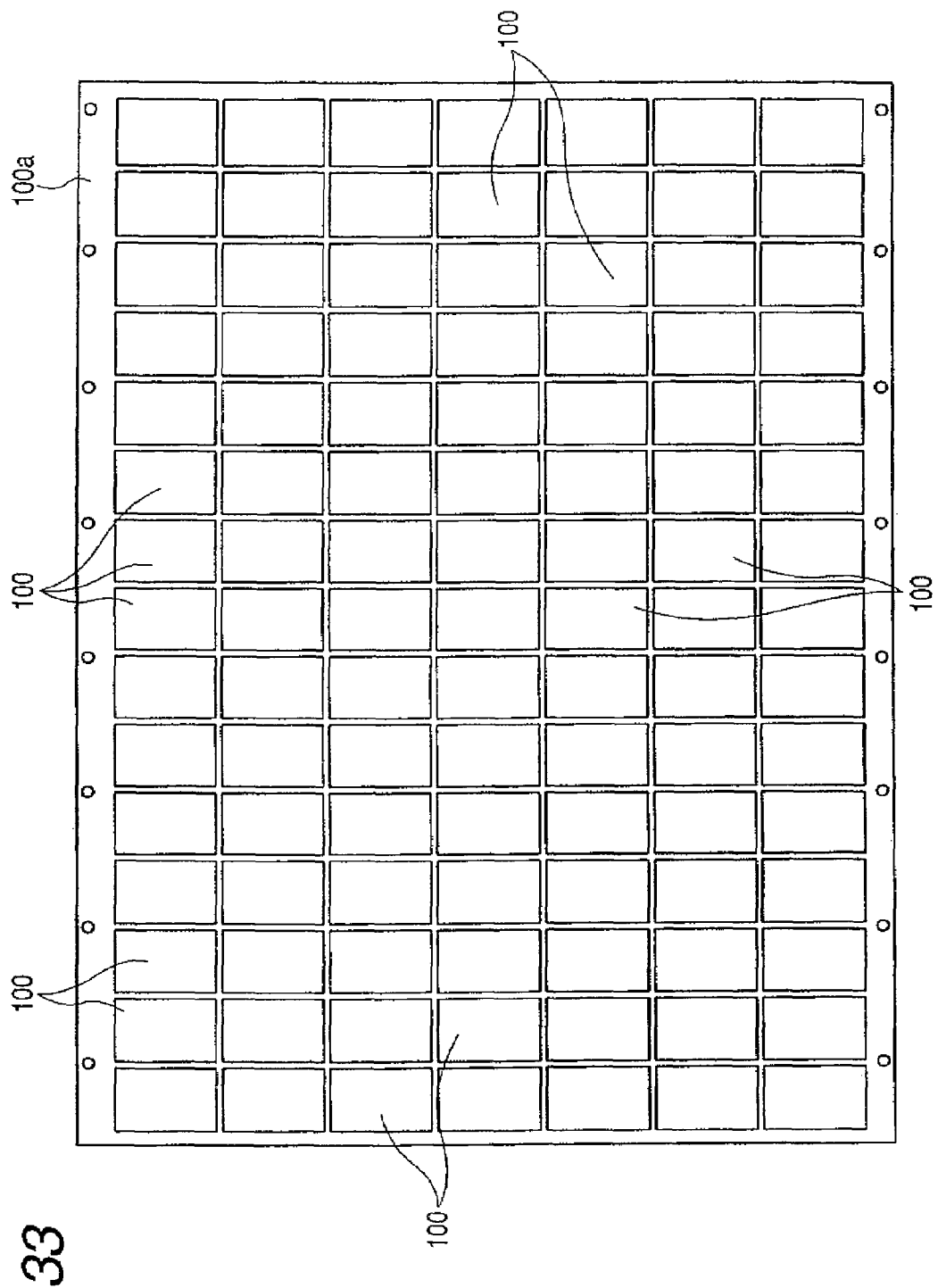
FIG. 33 is a diagram which shows a matrix substrate comprising plural connected substrates which are each to form one circuit part.
Figure 34:
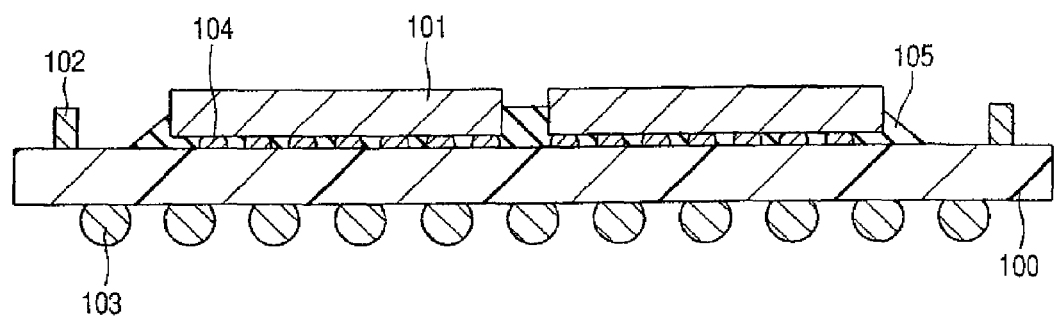
FIG. 34 is a cross-sectional view which shows a semiconductor integrated circuit device of MCM structure.
Figure 35:
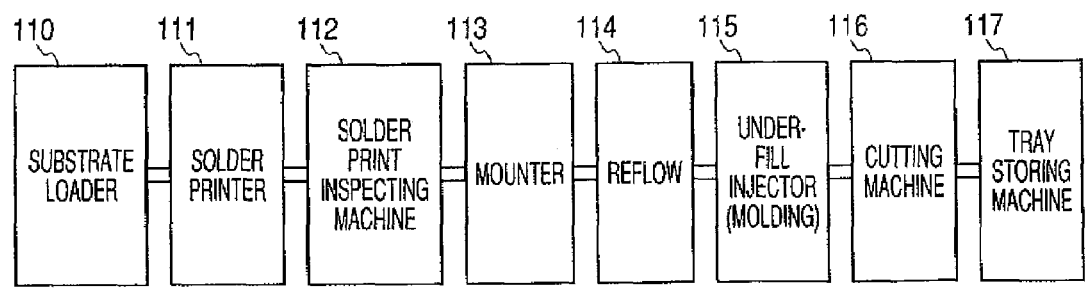
FIG. 35 is a block diagram showing a fabrication system for fabricating a semiconductor integrated circuit device.

Next, with reference to FIGS. 33 to 35, a description will be given of an example in which the 2D-3D solder print inspection system of this embodiment is applied to a semiconductor device manufacturing equipment. FIG. 33 shows a matrix substrate comprising plural connected substrates which each form one circuit part. FIG. 34 shows a semiconductor integrated circuit device of MCM structure, and FIG. 35 is a block diagram showing fabrication equipment for fabricating a semiconductor integrated circuit device.

Here, a description will be given of a semiconductor integrated circuit device in the form of a MCM (Multi Chip Module) as an example of an application of the 2D-3D solder print inspection system to the fabrication of a semiconductor device. As shown in FIG. 34, the MCM is a single functional part formed by mounting wafer chips 101, such as the foregoing BGAs (CSPs), and chip parts 102, such as the foregoing chip resistor and chip capacitor, onto a substrate 100, such as an organic multi-layer substrate of the same type as the foregoing substrate serving as an object of inspection or a ceramic multi-layer substrate. Solder balls 103 mounted on a back surface of the substrate 100 serve as terminals for external connection. In this MCM, an under-fill resin 105 is injected to the connection between solder bumps 104 on the wafer chips 101 and the substrate 100.

The same process as the substrate assembling process can be utilized for this manufacturing process. More specifically, first, creamy solder is printed onto the substrate 100, and then, this printed state is checked; and, if the printed state is good, the wafer chips 101 and the chip parts 102 are mounted, followed by heating the assembly by reflow to melt the creamy solder. Upon solidification of the thus-melted solder, an electric connection of the wafer chips 101 and the chip parts 102 with the substrate 100 is attained.

Since circuit parts are usually small in size, if they are subjected to processing one by one, the processing efficiency is poor. According to a method usually adopted for solving this problem, as shown in FIG. 33, a matrix substrate (plural substrates can be obtained by dividing a single substrate) 100a is used in which plural substrates 100, each forming one independent circuit part, are connected longitudinally and transversely.

Now, with reference to FIG. 35, a little more detailed description will be given about a process for fabricating a semiconductor integrated circuit device of MCM structure. First, a magazine with plural matrix substrates 100a set therein is set to a substrate loader 110. The substrate loader 110 delivers the substrates 100a one by one from the interior of the magazine to the next step. Then, in a solder printer 111, creamy solder is printed onto the substrate 100a.

Then, the foregoing principle of measuring the height and volume of printed solder, a positive method for detecting a height measurement reference in the measurement height and volume of printed solder, a method for preparing inspection data for measuring the height and volume of printed solder based on a pad upper surface, a method for measuring the height and volume of printed solder based on a pad upper surface while taking a measure against a warp condition of a substrate, and 3D solder print inspecting method suitable for visual determination, are used in a solder print inspecting machine 112 to determine whether the printed state of printed solder on each substrate 100 in the matrix substrate 100a is proper or not.

In this inspection, a part of each substrate 100, e.g., plural narrow portions, four corners and the central portion, closely adjacent pattern portions, connections of circuit parts and connector terminals, and portions where the applicability of creamy solder is poor, are inspected in three dimensions; and; thereafter; the whole surface of the substrate 100 is inspected in two dimensions, whereby print defects can be eliminated appropriately while enhancing the inspection efficiency as far as possible. Consequently, a high quality of printed solder is ensured, and the quality of the semiconductor device manufacturing process can be greatly improved.

Subsequently, the wafer chips 101 and the chip parts 102 are mounted on each substrate 100 in the matrix substrate 100a by means of a mounter 113. In FIG. 35, although only one mounter 113 is shown, the mounting of the wafer chips 101 and that of the chip parts 102 are generally performed separately by means of a flip-chip bonder and a high-speed chip mounter, respectively.

Further, the creamy solder is melted by heating by reflow 114 and the thus-melted solder solidifies while going through a subsequent cooling step, whereby the wafer chips 101 and the chip parts 102 are electrically connected to each substrate 100 in the matrix substrate 100a. Then, under-fill resin 105 is injected between the wafer chips 101 and the substrate 100 by means of an under-fill injector 115.

Then, the matrix substrate 100a is cut, substrate 100 by substrate 100, into individual semiconductor integrated circuit devices by means of a cutting machine 116. The thus-cut semiconductor integrated circuit devices are then stored one by one onto a tray by means of a tray storing machine 117. In this way, a semiconductor integrated circuit device of MCM structure, as shown in FIG. 34, is completed.

In the reflow step of the above-described process, if the amount of printed solder is small, the circuit parts and each substrate 100 will undergo a bonding defect; while, if the amount of printed solder is too large, a short-circuit will occur between adjacent electrodes (pads). In this embodiment, however, whether the creamy solder printed on the substrate 100 is proper or not is checked beforehand by means of the solder print inspecting machine 112, and only those substrates found to be proper flow to the next step, so that it is possible to prevent the occurrence of a fabrication defect caused by printed solder.

Although the present invention has been described above by way of various embodiments thereof, it goes without saying that the invention is not limited to the above-described embodiments, but that various changes may be made within the scope not departing from the gist of the invention.

The method of fabricating a semiconductor integrated circuit device according to the present invention is applicable particularly to an inspection process in which solder printed on a substrate is subjected to 3D and 2D inspections by means of a solder print inspection system, and it is further applicable widely to various types of solder printing machines for printing solder onto a substrate, which machines have a printed solder inspecting function.

What is claimed is:

1. A method of fabricating a semiconductor device, comprising the steps of:
   (a) preparing a wiring substrate having plural wiring patterns, pad patterns, and a solder resist layer on one surface thereof, said plural wiring patterns being covered by said solder resist layer, said pad patterns being exposed from by said solder resist layer;
   (b) configuring a reference plane over said pad patterns by subjecting said wiring substrate to a three-dimensional measurement, to measure an actual height of solder which is to be formed on each of said pad patterns in a subsequent process;
   (c) after the step (b), printing solder on said wiring substrate, to form solder patterns on said pad patterns respectively;
   (d) after the step (c), inspecting height of said solder patterns printed over the substrate with reference to said reference plane; and
   (e) after the step (d), mounting circuit parts over said one surface of said wiring substrate by using said solder patterns.

2. A method of fabricating a semiconductor device according to claim 1, wherein said reference plane corresponds to an upper surface of said solder resist layer.

3. A method of fabricating a semiconductor device according to claim 2, wherein said solder resist layer has a first portion and a second portion,
   wherein said first and second portions have different heights from upper surfaces of said pad patterns corresponding to said first and second portions of said solder resist layer respectively, and
   wherein said reference plane includes said different heights.

4. A method of fabricating a semiconductor device according to claim 3, wherein said circuit parts include a semiconductor package.

5. A method of fabricating a semiconductor device according to claim 4, wherein said semiconductor package has a plurality of leads, and wherein the step (e) includes subjecting said wiring substrate to a heat treatment to solder said plurality of leads of said semiconductor package to said pad patterns of said wiring substrate.

6. A method of fabricating a semiconductor device, comprising the steps of:
   (a) preparing a wiring substrate having plural wiring patterns, pad patterns, and a solder resist layer on one surface thereof, using a wiring substrate fabrication system, said plural wiring patterns being covered by said solder resist layer, said pad patterns being exposed from by said solder resist layer;
   (b) configuring a reference plane over said pad patterns by subjecting said wiring substrate to a three-dimensional measurement by a 3D measurement system, to measure an actual height of solder which is to be formed on each of said pad patterns in a subsequent process;
   (c) after the step (b), printing solder on said wiring substrate by a solder printing system, to form solder patterns on said pad patterns respectively;
   (d) after the step (c), inspecting height of said solder patterns printed over the substrate with reference to said reference plane, using an inspection apparatus; and
   (e) after the step (d), and utilizing a circuit part mounting system, mounting circuit parts over said one surface of said wiring substrate using said solder patterns.

* * * * *